(12) United States Patent
Kremer et al.

(10) Patent No.: US 7,517,686 B2
(45) Date of Patent: Apr. 14, 2009

(54) DEDIFFERENTIATED, PROGRAMMABLE STEM CELLS OF MONOCYTIC ORIGIN, AND THEIR PRODUCTION AND USE

(75) Inventors: Bernd Karl Friedrich Kremer, Kiel (DE); Fred Fändrich, Kiel (DE); Maren née Schulze Ruhnke, Kiel (DE)

(73) Assignee: Blasticon Biotechnologische Forschung GmbH, Kiel (DE)

( * ) Notice: Subject to any disclaimer, the term of this patent is extended or adjusted under 35 U.S.C. 154(b) by 388 days.

(21) Appl. No.: 11/282,684

(22) Filed: Nov. 21, 2005

(65) Prior Publication Data

US 2006/0078989 A1    Apr. 13, 2006

Related U.S. Application Data

(60) Division of application No. 10/401,026, filed on Mar. 28, 2003, now Pat. No. 7,138,275, which is a continuation-in-part of application No. 10/372,657, filed on Feb. 25, 2003, now abandoned.

(30) Foreign Application Priority Data

Mar. 28, 2002   (DE)   ................................ 102 14 095
Feb. 25, 2003   (WO)   ...................... PCT/EP03/02121

(51) Int. Cl.
    *C12N 5/00*   (2006.01)
(52) U.S. Cl. ....................... 435/377; 435/375; 435/325
(58) Field of Classification Search ........................ None
    See application file for complete search history.

(56) References Cited

U.S. PATENT DOCUMENTS

| 5,650,309 A | 7/1997 | Wong-Staal et al. |
| 6,090,625 A | 7/2000 | Abuljadayel |
| 6,294,381 B1 | 9/2001 | Olweus et al. |
| 7,112,440 B2 | 9/2006 | Abuljadayel |
| 7,220,412 B2 | 5/2007 | Abuljadayel |
| 2001/0049139 A1 | 12/2001 | Lagasse et al. |
| 2002/0028510 A1 | 3/2002 | Sanberg et al. |
| 2003/0166272 A1 | 9/2003 | Abuljadayel |
| 2004/0136973 A1 | 7/2004 | Huberman et al. |

FOREIGN PATENT DOCUMENTS

| WO | WO 98/53048 A1 | 11/1998 |
| WO | WO 00/70022 A2 | 11/2000 |
| WO | WO 02/14469 A2 | 2/2002 |
| WO | WO 2004/043990 A2 | 5/2004 |

OTHER PUBLICATIONS

Thomas CD, ed. 1997. Taber's Cyclopedic Medical Dictionary, 18th Ed. p. 1229.*
Roufosse CA et al. 2004. Circulating mesenchymal stem cells. Int J Biochemistry Cell Biol 36:585-597.*
Pittenger MF et al. 1999. Multilineage potential of adult human mesenchymal stem cells. Science 284:143-147.*
Lopez M et al. 1993. Autologous lymphocytes prevent the death of monocytes in culture and promote, as do GM-CSF, IL-3, and M-CSF, their differentiation into macrophages. J Immunol Methods 159: 29-38.*
U.S. Appl. No. 09/568,254, filed May 2000, Abuljadayel.
Alberts et al., *Molecular Biology of the Cell*, Third Edition, Chapter 22, pp. 1168-1169 (1989), U.S. Appl. No. 10/401,026.
Brossart et al., "Generation of Functional Human Dendritic Cells from Adherent Peripheral Blood Monocytes by CD40 Ligation in the Absence of Granulocyte-Macrophase Colony-Stimulating Factor in Supporting Monocyte Differentiation in Culture", *Blood*, 92(11):4238-4247 (1998).
Donovan et al., "The End of the Beginning for Pluripotent Stem Cells," *Nature*, 414:92-97 (Nov. 2001), U.S. Appl. No. 10/401,026.
Gotz et al., "Flt3$^{high}$ and Flt3$^{low}$ CD34$^+$ Progenitor Cells Isolated From Human Bone Marrow are Functionally Distinct", *Blood*, 91(6):1947-1958 (1998), U.S. Appl. No. 10/401,026.
International Search Report from International Application No. PCT/EP03/02121 (WO 03/083091 A1), issued Jun. 18, 2003, U.S. Appl. No. 10/401,026.
International Search Report from International Application No. PCT/EP03/03279 (WO 03/083092 A1), issued Aug. 25, 2003, U.S. Appl. No. 10/401,026.
Lucas et al., "Self-Renewal, Maturation, and Differentiation of the Rat Myelomonocytic Hematopoietic Stem Cell," *The FASEB Journal*, 13:263-272 (Feb. 1999), U.S. Appl. No. 10/401,026.
Ruhnke et al., "Differentiation of in Vitro-Modified Human Peripheral Blood Monocytes into Hepatocyte-like and Pancreatic Islet-like Cells", *Gastroenterology*, 128(7):1774-1786 (Jun. 2005), U.S. Appl. No. 10/401,026.
Sorg et al., "Phenotypic and Functional Comparison of Monocytes from Cord Blood and Granulocyte Colony-Stimulating Factor-Mobolized Apheresis Products", *Experimental Hematology*, 29:1289-1294 (2001), U.S. Appl. No. 10/401,026.
Terskikh et al., "Gene Expression Analysis of Purified Hematopoietic Stem Cells and Committed Progenitors", *Blood*, 102(1):94-191 (Jul. 2003), U.S. Appl. No. 10/401,026.
Weissman, "Stem Cells: Units of Development, Units of Regeneration, and Units in Evolution," *Cell*, 100:157-168 (Jan. 2000), U.S. Appl. No. 10/401,026.
Weissman, "Translating Stem and Progenitor Cell Biology to the Clinic: Barriers and Opportunities," *Science*, 287:1442-1446 (Feb. 2000), U.S. Appl. No. 10/401,026.
Young et al., *Journal of Immunology*, vol. 145, No. 2, p. 607-615. STN Biosis abstract, acccession No. 1990:416907, U.S. Appl. No. 10/401,026.

(Continued)

*Primary Examiner*—Lora E Barnhart
(74) *Attorney, Agent, or Firm*—Arnold & Porter LLP

(57) ABSTRACT

The invention relates to the production of adult dedifferentiated, programmable stem cells from human monocytes by cultivation of monocytes in a culture medium which contains M-CSF and IL-3. The invention further relates to pharmaceutical preparations, which contain the dedifferentiated, programmable stem cells and the use of these stem cells for the production of target cells and target tissue.

22 Claims, 15 Drawing Sheets

OTHER PUBLICATIONS

Andreesen et al., "Adoptive Transfer of Tumor Cytotoxic Macrophages Generated in Vitro from Circulating Blood Monocytes: A New Approach to Cancer Immunotherapy", *Cancer Research*, 50:7450-7456 (1990).

Grill et al., "2-Mercaptoethanol is a survival factor for olfactory, cortical and hippocampal neurons in short-term dissociated cell culture", *Brain Res.*, 613(1):168-72 (1993).

Ishii et al., "Mechanism of growth promotion of mouse lymphoma L1210 cvells in vitro by feeder layer or 2-mercaptoethanol", *J Cell Physiol*, 107(2):283-93 (1981).

Ishii et al., "Mechanism of growth stimulation of L1210 cells by 2-mercaptoethanol in vitro: Role of the mixed disulfide of 2-mercaptoethanol and cysteine", *J Biol Chem*, 256(23):12387-92 (1981).

Pruett et al., "Involvement and relative importance of at least two distinct mechanisms in the effects of 2-mercaptoethanol on murine lymphocytes in culture", *J Cell Physiol* 141(1):40-5 (1989).

* cited by examiner

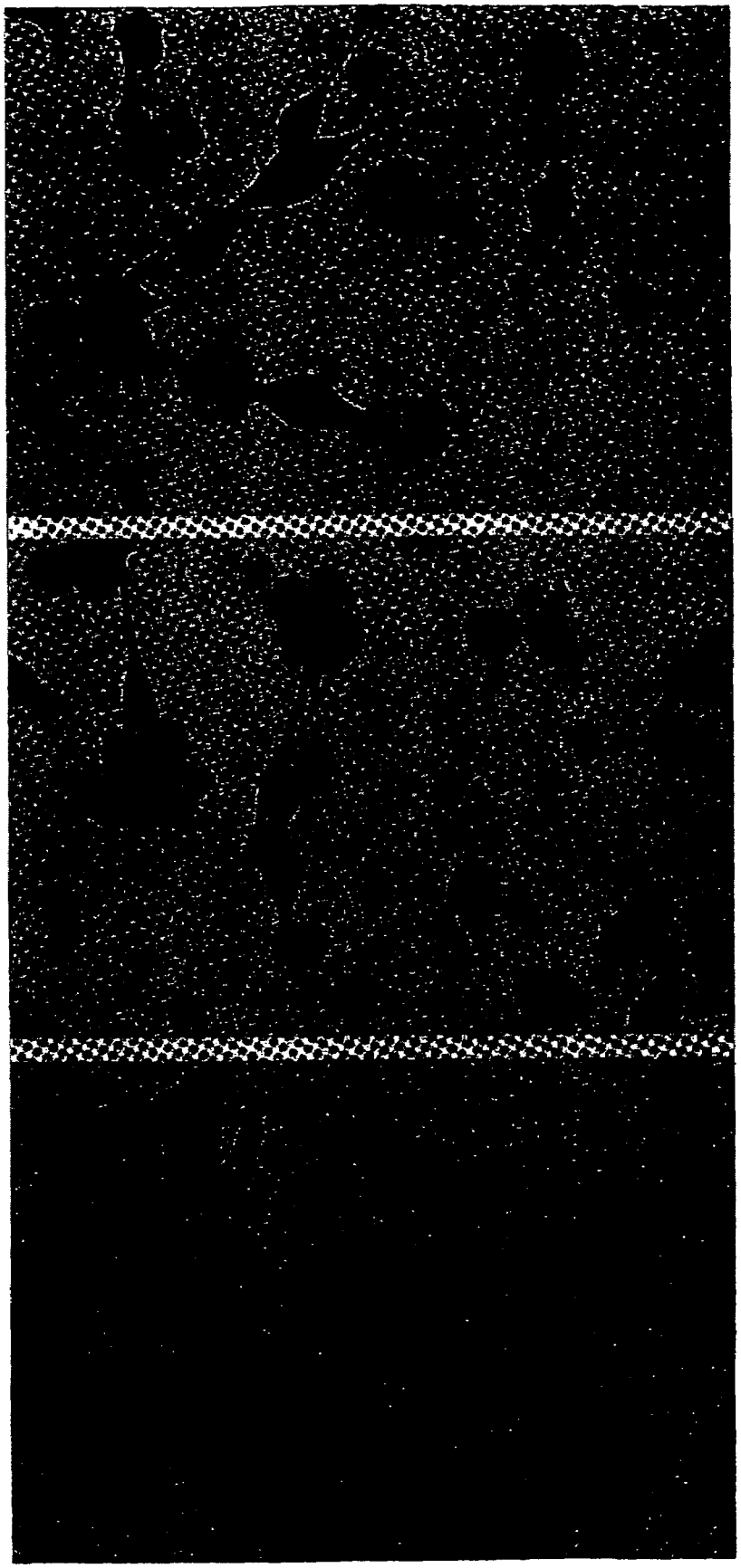
Fig.1 Differentiation into neurons and glia cells

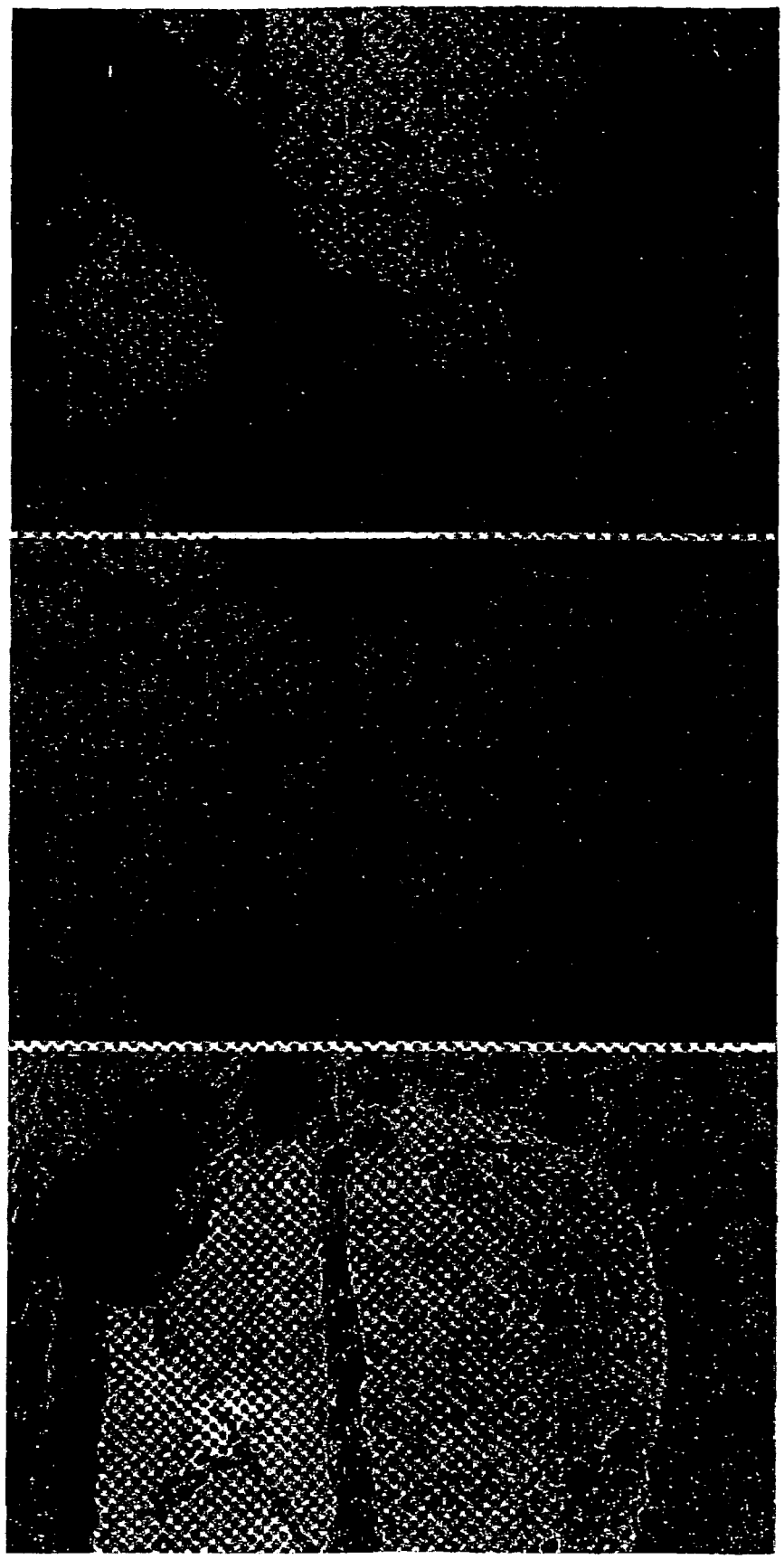
Fig.2 Differentiation into endothelial cells

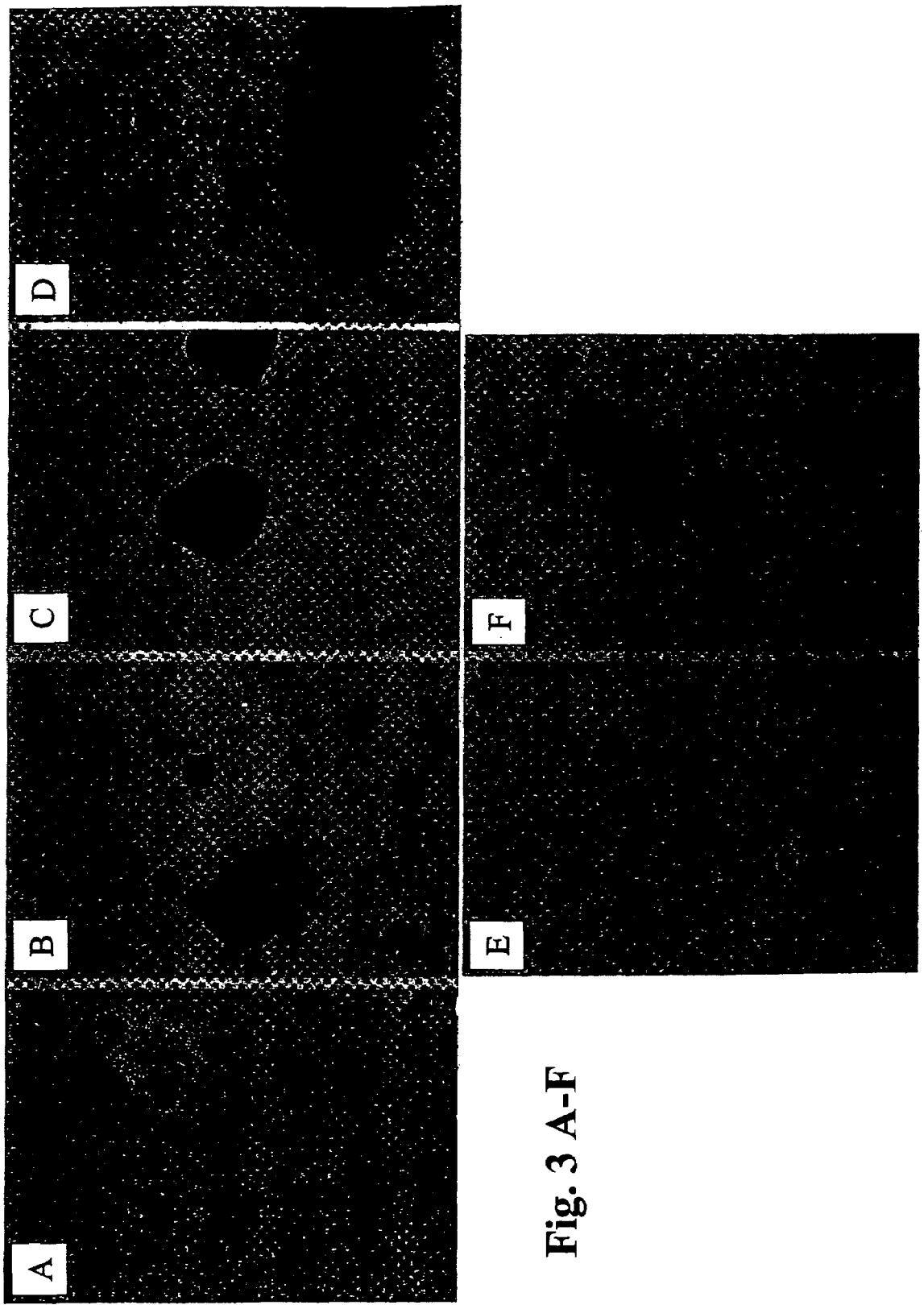
Fig. 3 A-F

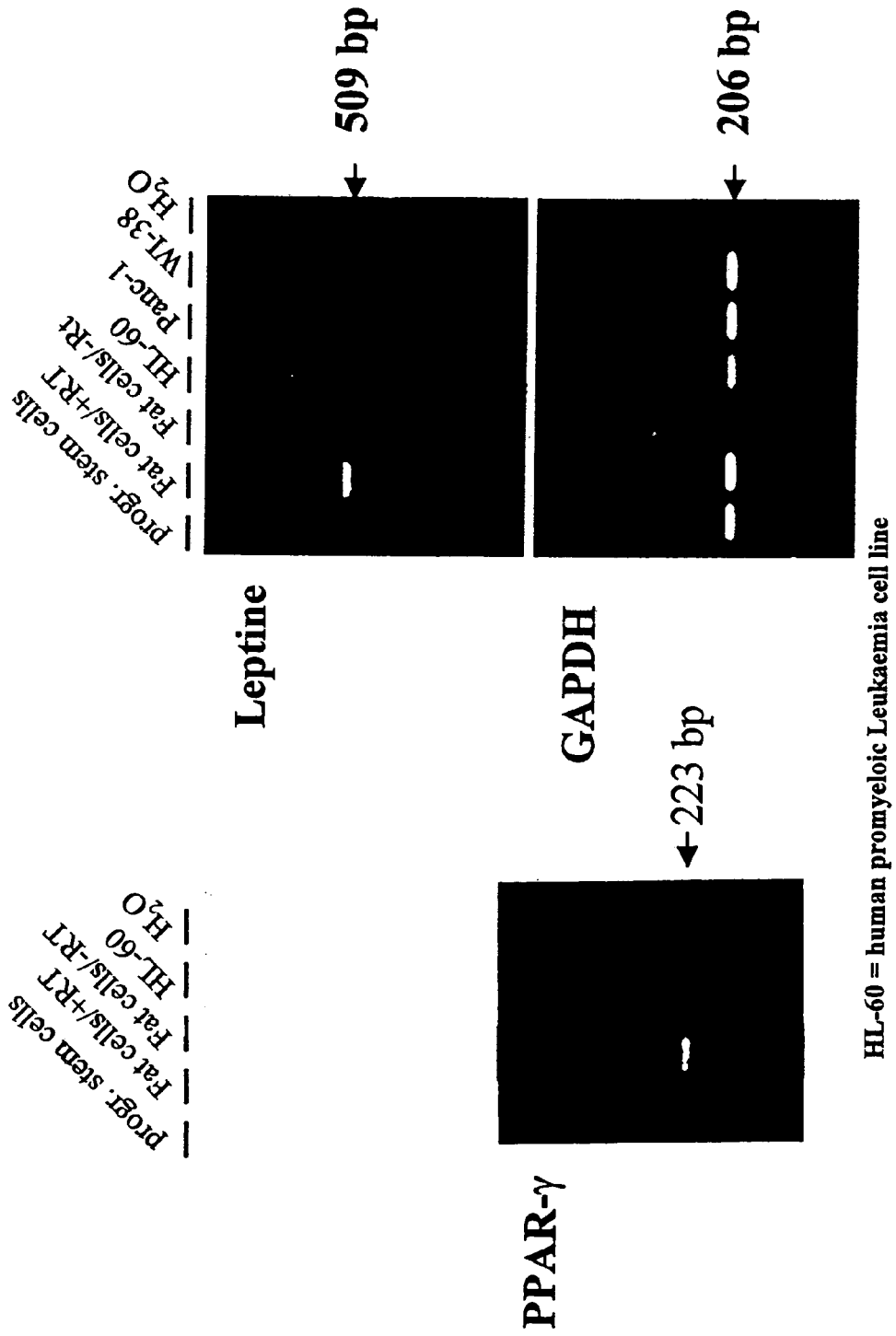

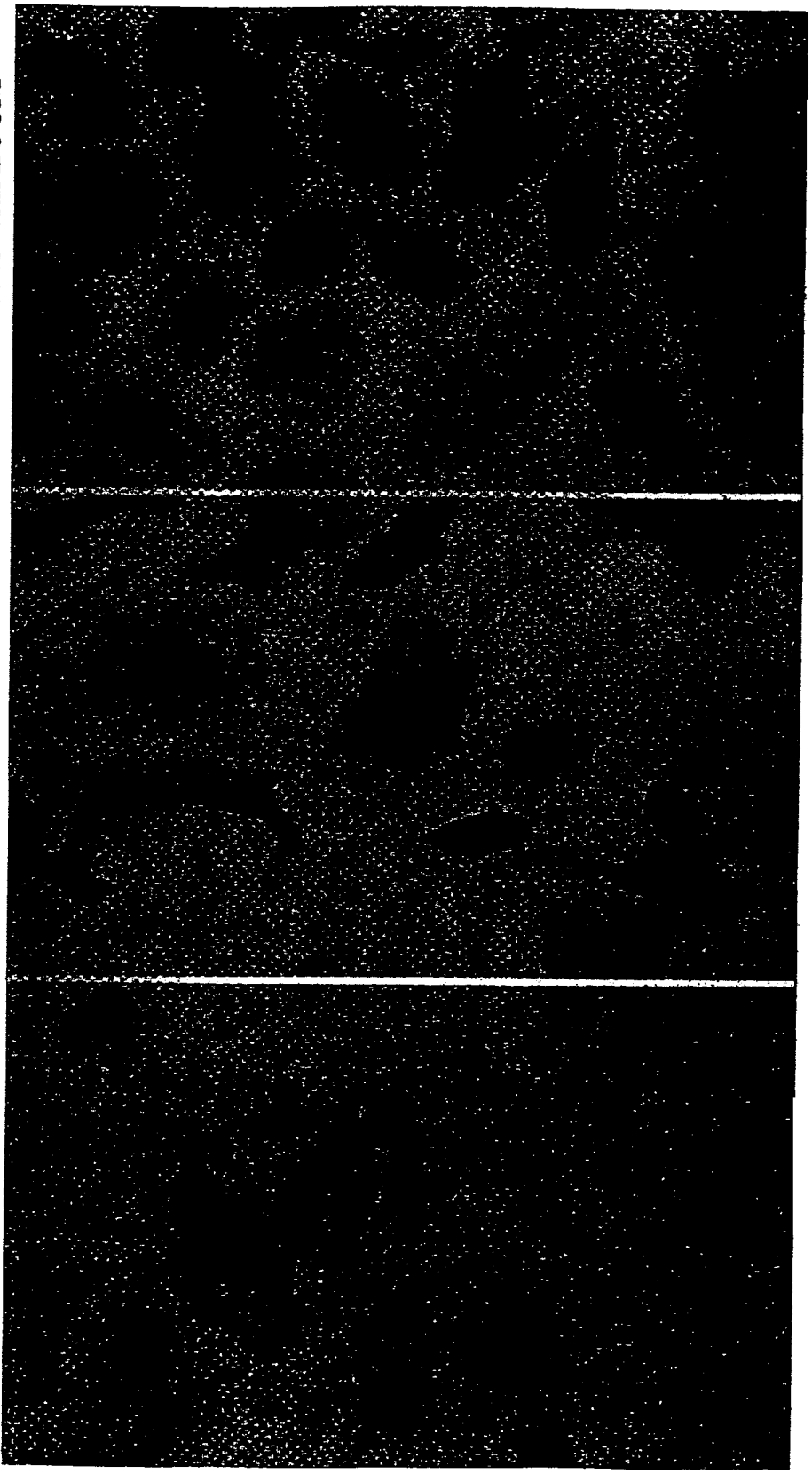
Fig. 4A: day 6 after cultivation of the stem cells with LCGM
Fig. 4B: day 10 after cultivation of the stem cells with LCGM
Fig. 4C: day 12 after cultivation of the stem cells with LCGM
Alpha-fetoprotein-positive hepatocytes derived from programmable stem cells of monocytic origin

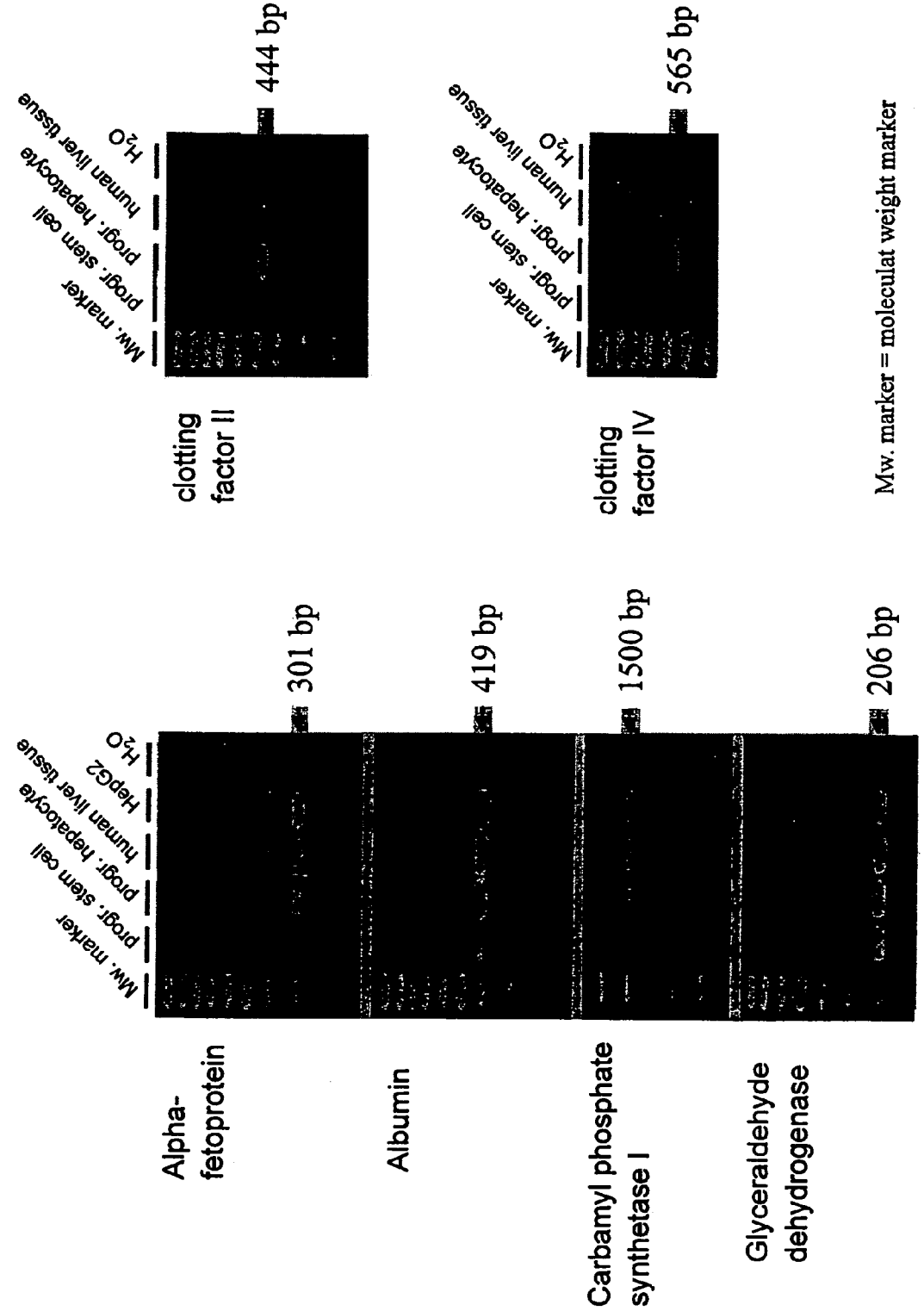
Fig. 4D RT-PCR analysis of hepatocyte-specific genes in programmable stem cells and programmed hepatocytes

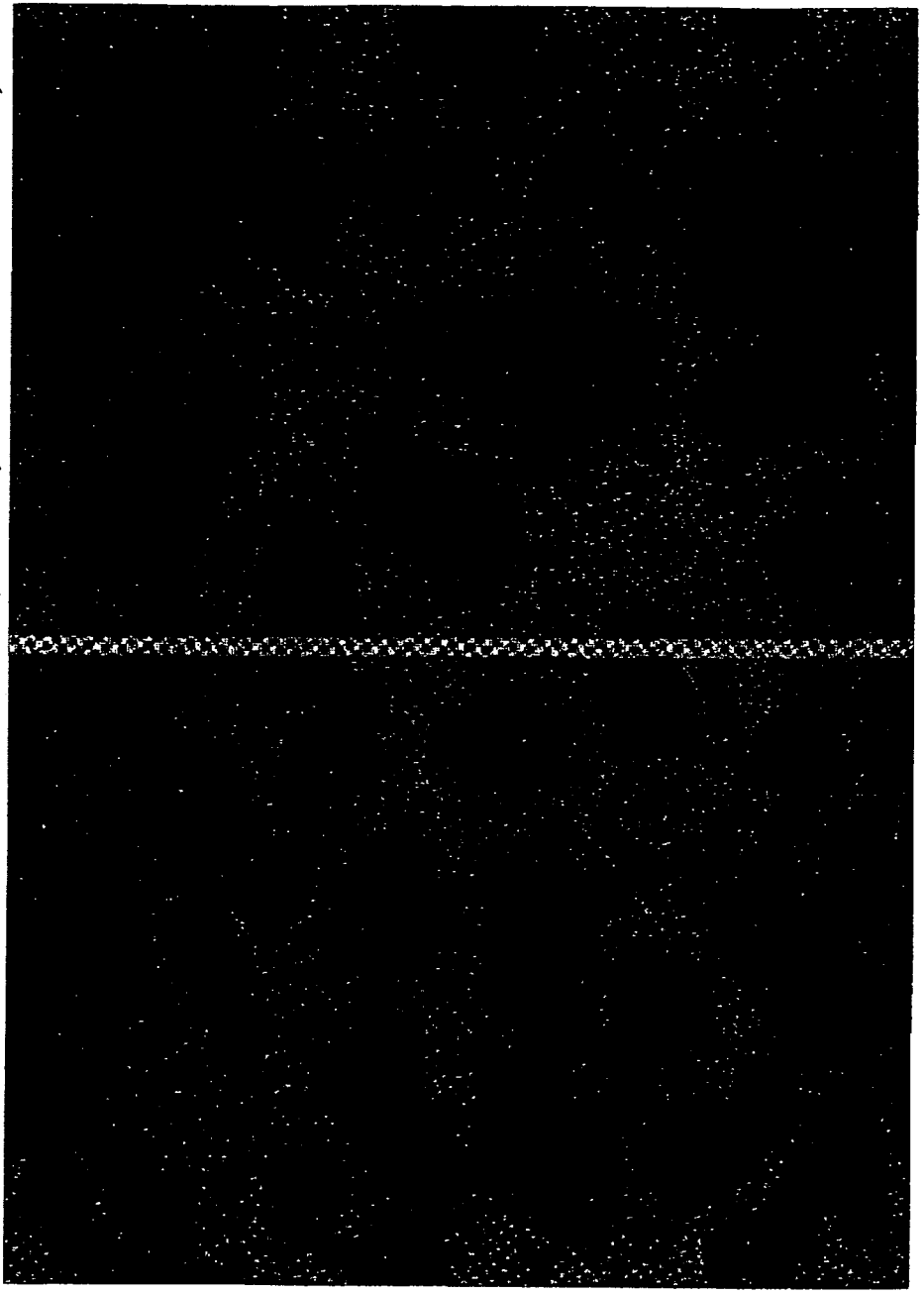
Cytokeratin 5 and 6 positive keratinocytes derived from programmable stem cells of monocytic origin
Fig. 5A: day 6 after treatment with KCGM (keratinocyte cell conditioned medium)
Fig. 5B: day 10 after treatment with KCGM (keratinocyte cell conditioned medium)

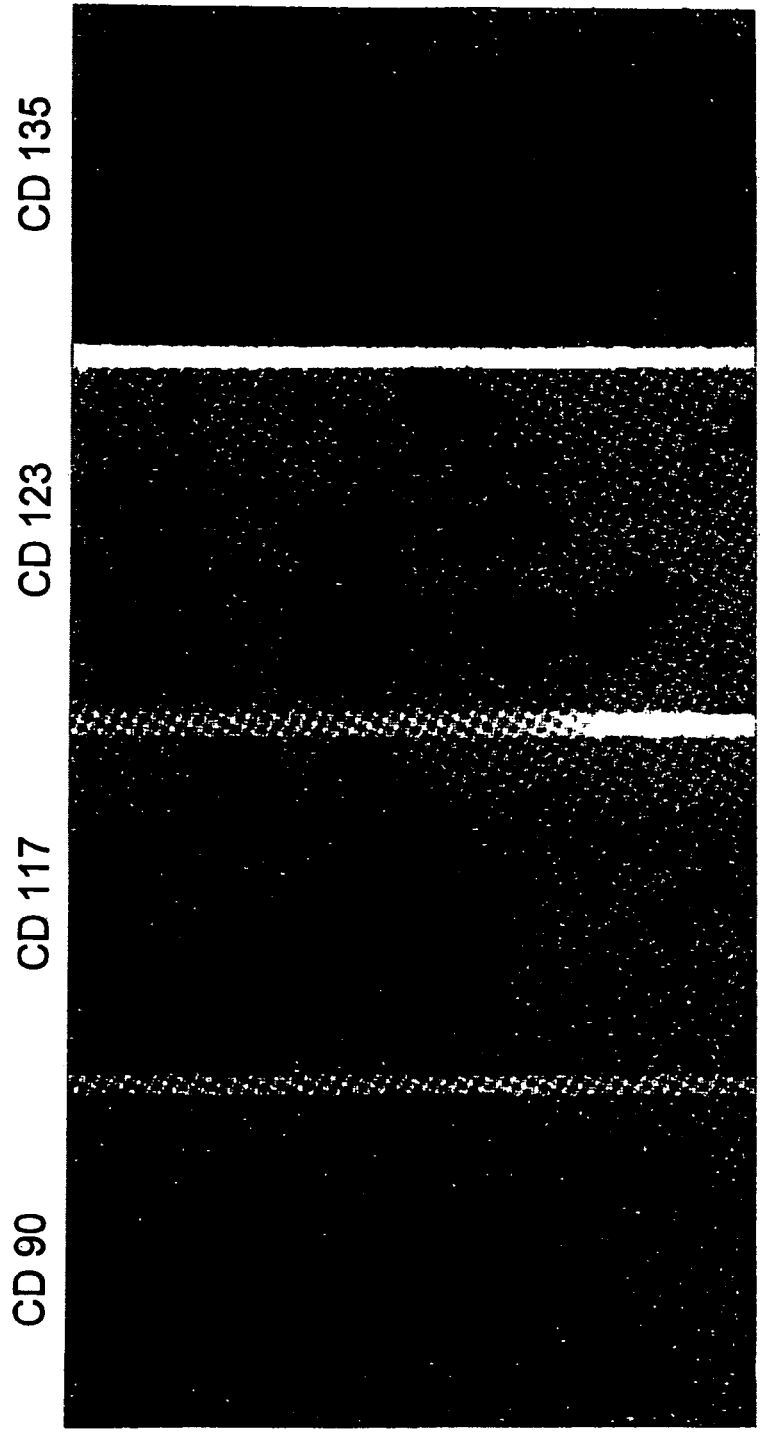
Fig. 6 Stem cell marker of dedifferentiated programmable stem cells of monocytic origin
The dedifferentiated programmable stem cells derived according to the specification show clearly positive CD117 expression and strongly positive expression of the stem cell markers CD90, CD123 and CD135

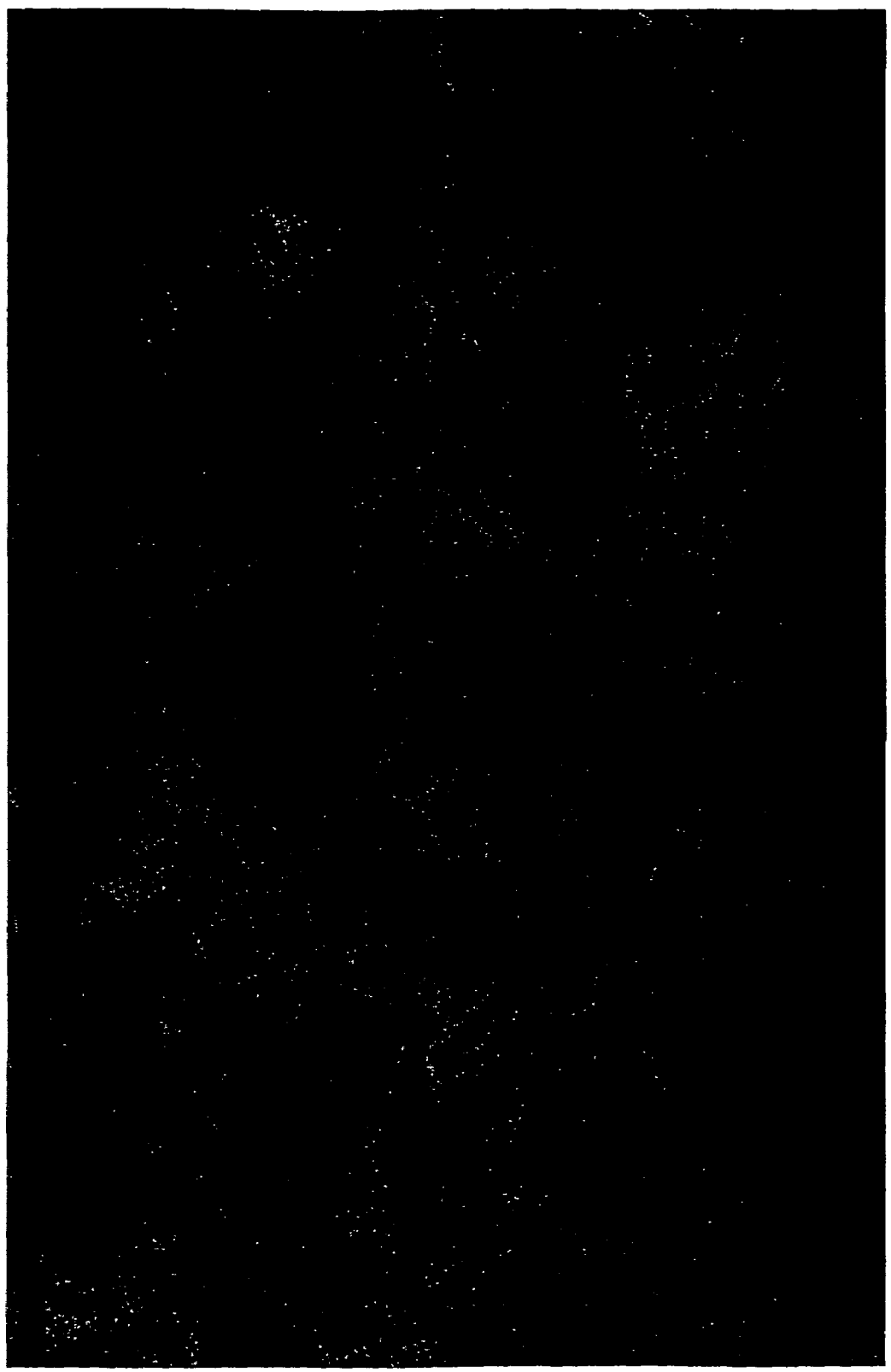
Fig. 7A: FISH Y chromosome detection in stem cells derived hepatocytes

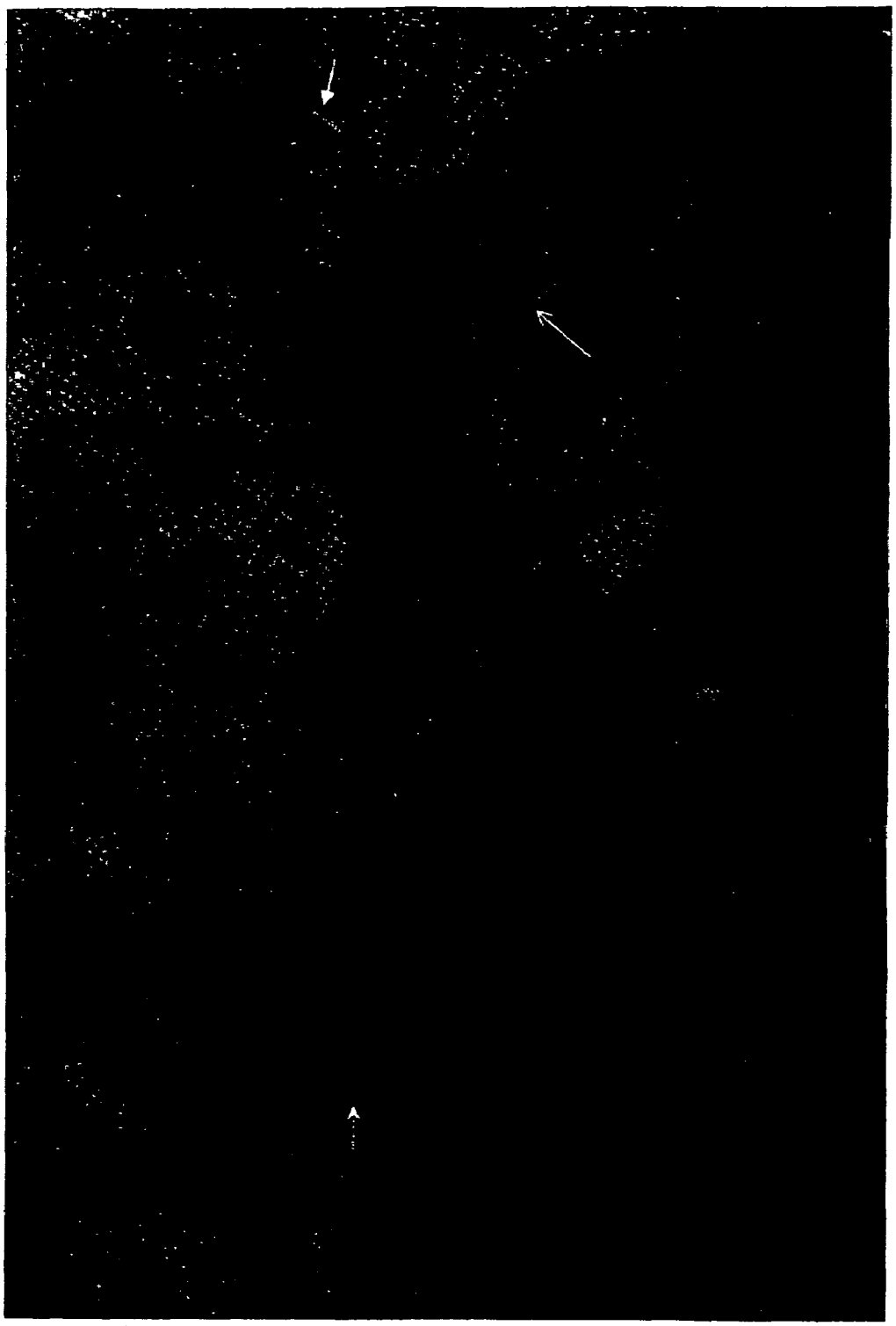
Fig. 7B: FISH Y chromosome detection in stem cells derived hepatocytes (↑), endothelial cells (↑) and bile duct epithelial cells (↑)

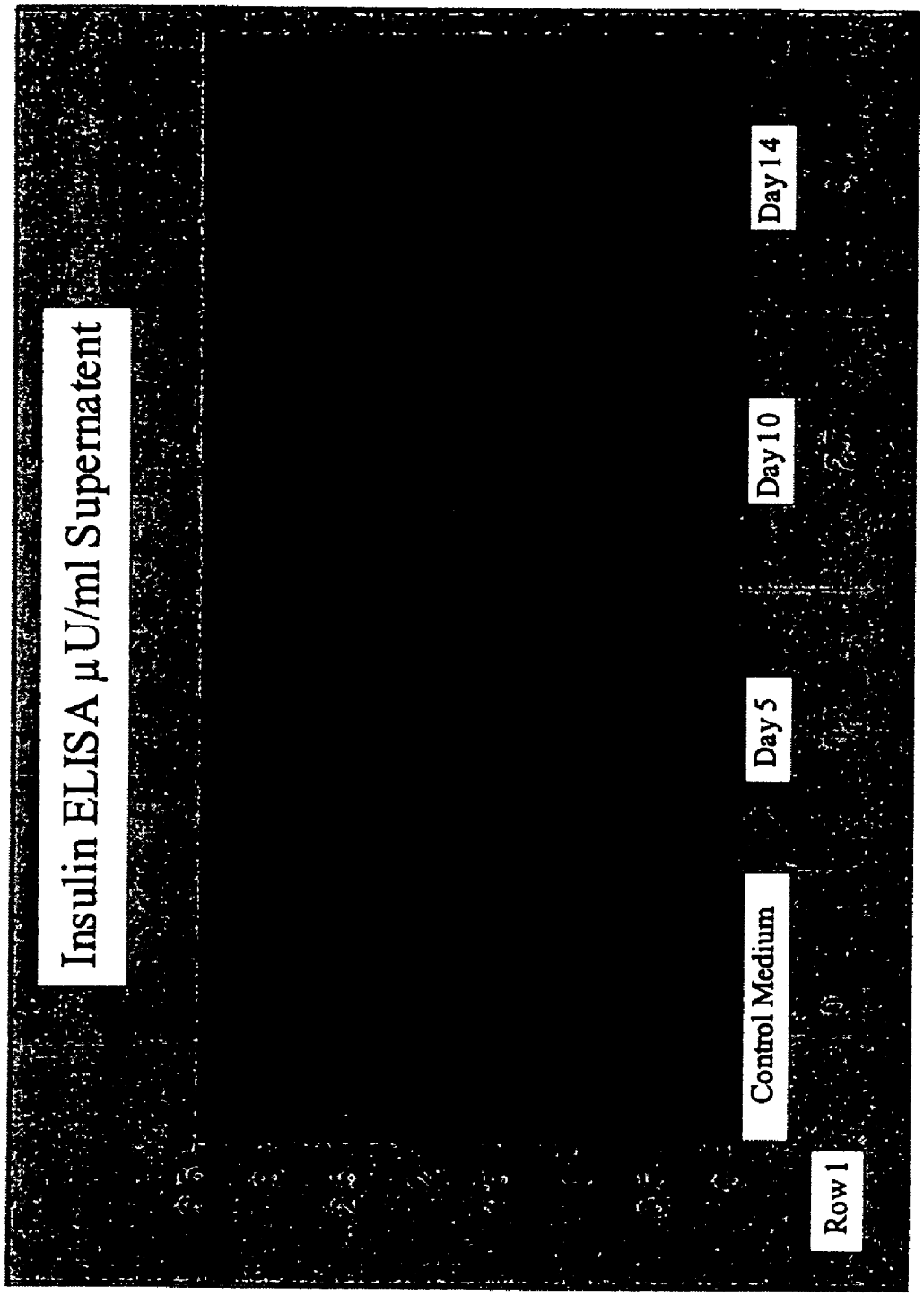
Fig. 8: Insulin producing Cells

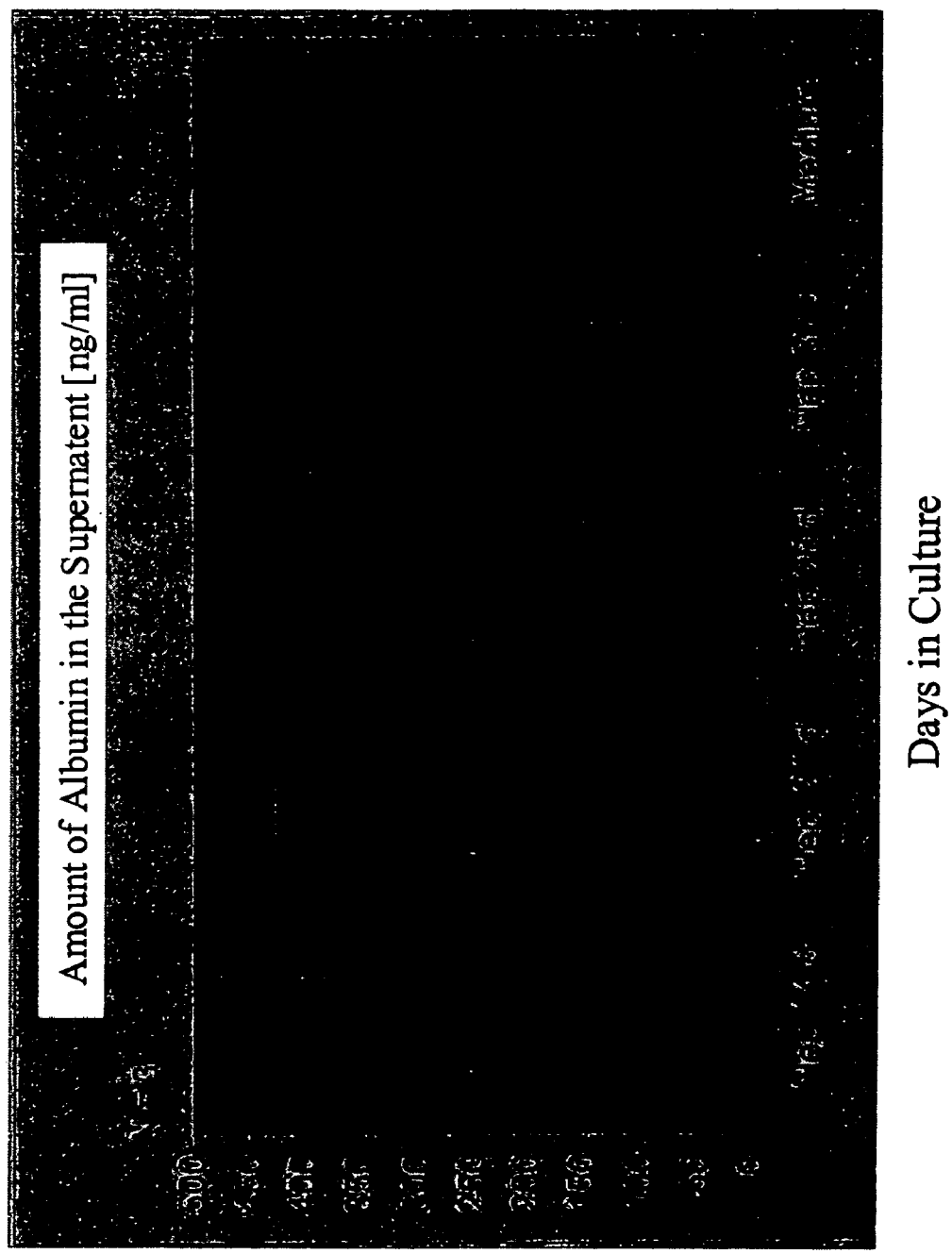
Fig. 9: Albumin Production of Hepatocyte like Cells Time Course

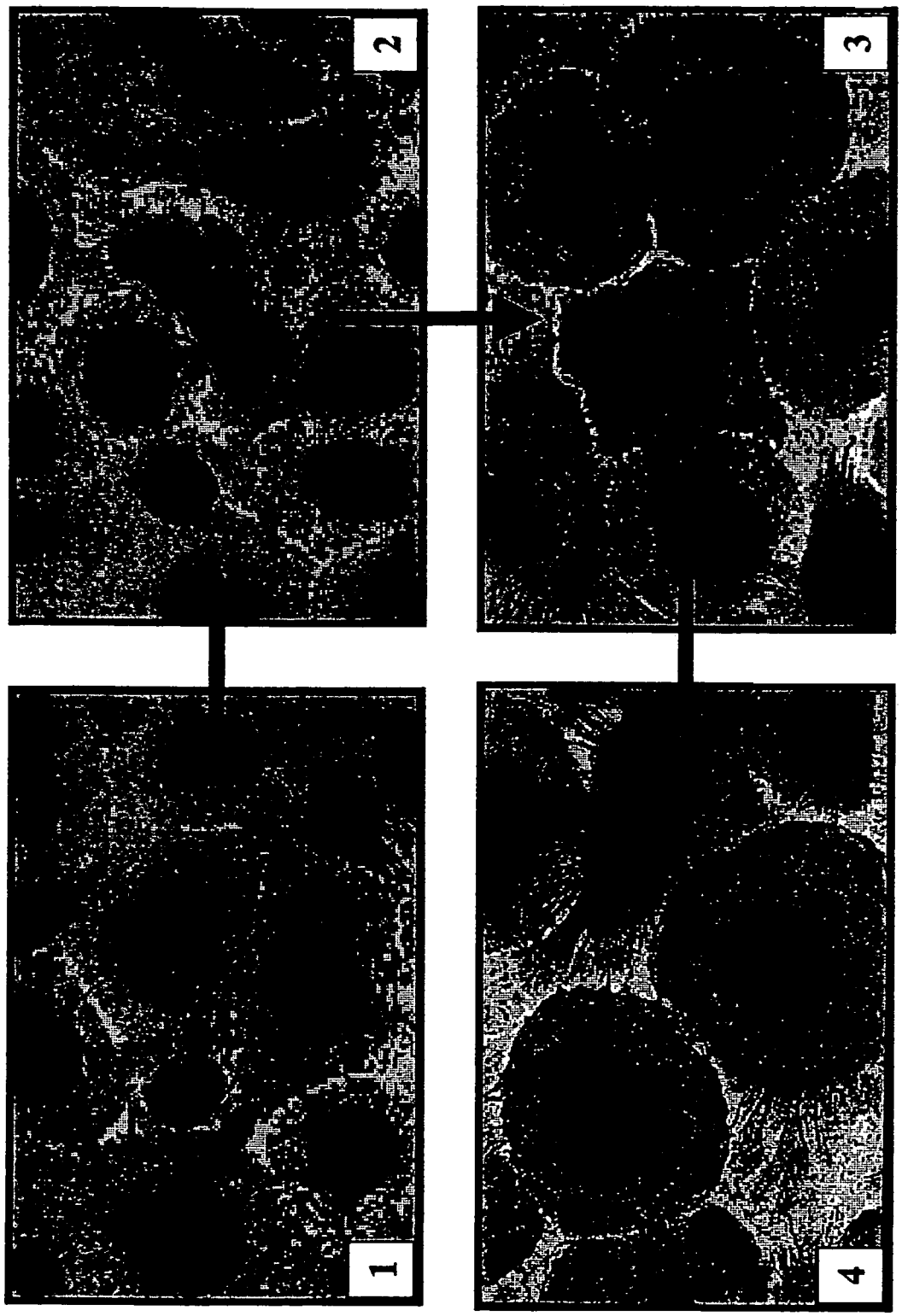
Fig. 10: Hepatocytes derived from Monocytes

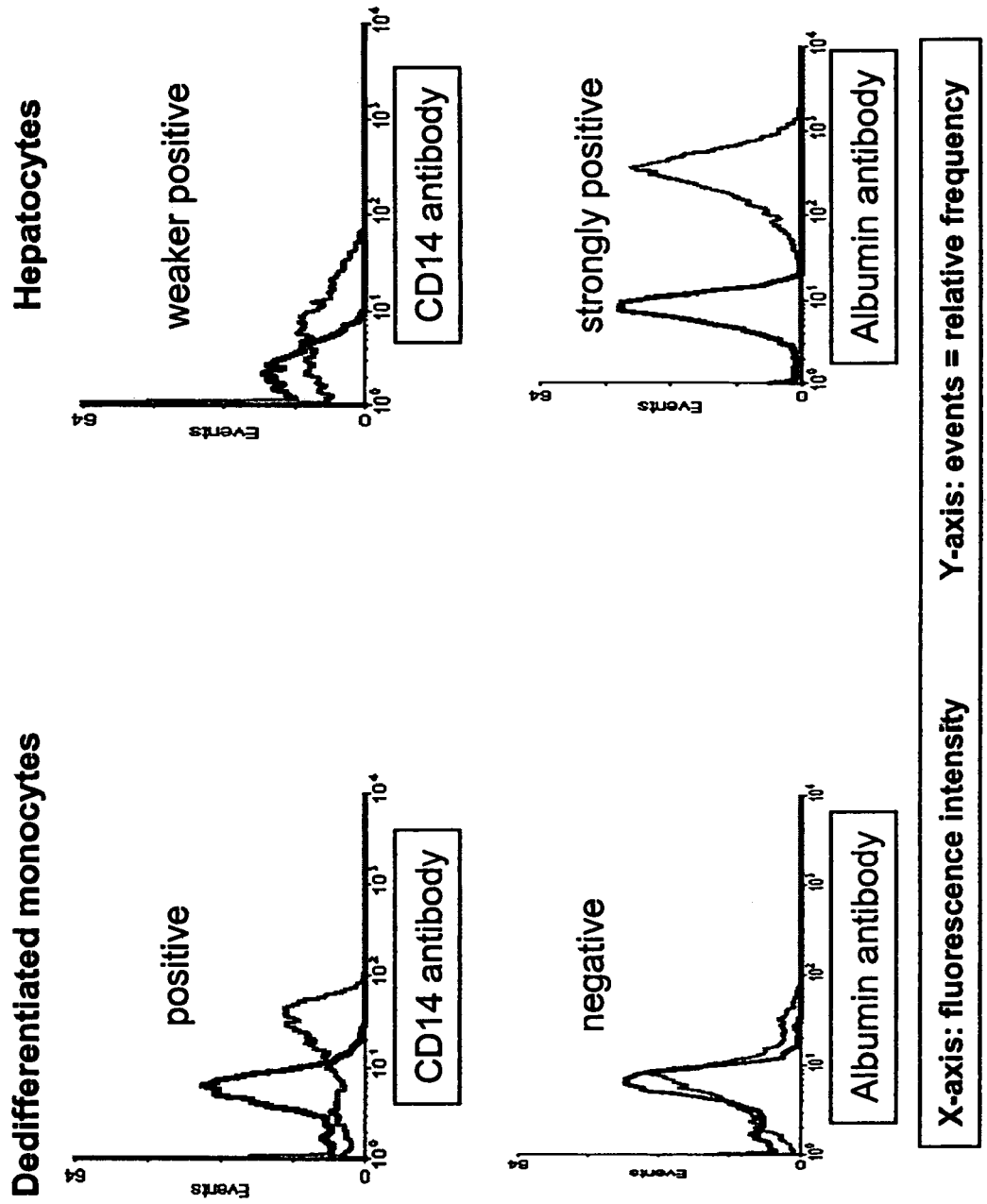
Fig. 11: FACS Analysis

DEDIFFERENTIATED, PROGRAMMABLE STEM CELLS OF MONOCYTIC ORIGIN, AND THEIR PRODUCTION AND USE

CROSS REFERENCE TO RELATED APPLICATIONS

This application claims the benefit under 35 U.S.C. § 120 as a divisional application of U.S. application Ser. No. 10/401,026, filed Mar. 28, 2003, issued as U.S. Pat. No. 7,138,275 on Nov. 21, 2006, which is a continuation-in-part of U.S. application Ser. No. 10/372,657, filed Feb. 25, 2003 (abandoned), which claims benefit under 35 U.S.C. § 119 of German Patent Application No. 102 14 095.2, filed Mar. 28, 2002 and claims benefit under 35 U.S.C. § 365 of International Application No. PCT/EP03/02121 filed Feb. 25, 2003, which claims the benefit of German Patent Application Number 102 14 095.2, filed Mar. 28, 2002. The disclosures of these applications are hereby incorporated by reference in their entirety.

BACKGROUND OF THE INVENTION

The term "stem cells" designates cells which (a) have the capability of self-renewal and (b) the capability to form at least one and often a number of specialized cell types due to their asymmetrical division capability (cf. Donovan, P. J., Gearhart, J., Nature 414: 92-97 (2001)). The term "pluripotent" designates stem cells, which can essentially be differentiated into all possible cell types of the human and animal body. Such stem cells have hitherto only been obtainable from embryonic tissue or embryonic carcinoma (testicular tumor) (cf: Donovan, P. J., Gearhart, J., loc cit). The use of embryonic stem cells has been the subject of extensive public discussion, especially in Germany, and is regarded as extremely problematical. Besides the ethical and legal problems connected with embryonic stem cells, the therapeutic use of such cells also comes up against difficulties. By nature, embryonic stem cells are obtained from donor organisms, which are heterologous vis-á-vis the potential recipients of differentiated cells or tissue (hereafter referred to as somatic target cells or target tissue) developed from these cells. It is therefore to be expected, that such target cells will trigger an immediate immunological response in the potential recipients in the form of rejection.

Stem cells can be also isolated from different tissues of adult, i.e., from differentiated individuals. Such stem cells are referred to in the state of the art as "multipotent adult stem cells". In the body they play a role in tissue regeneration and homeostasis. The essential difference between embryonic pluripotent stem cells and adult multipotent stem cells lies in the number of differentiated tissues, which can be obtained from the respective cells. Presumably, this is due to the fact that pluripotent stem cells come from sperm cells, or from cells which can produce sperm, while adult multipotent stem cells come from the body or soma of adult individuals (cf. Donovan, P. J., Gearhart, J., loc cit, Page 94), which are not capable of sperm production.

The actual problems relating to the obtaining and use of adult stem cells however lie in the rarity of these cells. Thus, in the bone marrow, stem cells are present only in the ratio of 1:10,000, in the peripheral blood of 1:250,000 and in the liver in the ratio of 1:100,000. Obtaining such stem cells is therefore very expensive and stressful for the patient. In addition the generation of large cell quantities, as required for clinical therapy, has scarcely been possible hitherto at reasonable expense.

This is contrasted by a constantly increasing need for possibilities for treatment of destroyed tissue in the form of "tissue engineering" or as cell therapy, within the framework of which skin-, muscle-, heart muscle-, liver-, islet-, nerve-, neurone-, bone-, cartilage-, endothelium- and fat cells etc. are to be replaced.

In this connection, the foreseeable development of the age and disease profile of the population in the western world is decisive, leading to the expectation of a drastic turning point in the next 10 years in the health and care sector of the western European population, including the USA and Canada. In the Federal Republic of Germany alone, the demographic development suggests a 21%-growth in population in the 45-64 year-old age group by 2015, and a 26%-growth in the over-65 age group. This is bound to result in a change in patient structure and in the spectrum of diseases requiring treatment. Predictably, diseases of the cardio-circulatory system (high pressure, myocardial infarction), vascular diseases due to arteriosclerosis and metabolic diseases, metabolic diseases such an diabetes mellitus, diseases at liver metabolism, kidney diseases as well as diseases of the skeletal system caused by age-related degeneration, and degenerative diseases of the cerebrum caused by neuronal and glial cell losses will increase and require innovative treatment concepts.

These facts explain the immense national and international research and development efforts by the specialists involved, to obtain stem cells which can be programmed into differentiated cells typical of tissue (liver, bone, cartilage, muscle, skin etc.).

The problem underlying the invention therefore resides in making available adult stem cells, the generation of which gives rise to no ethical and/or legal problems, which are rapidly available for the planned therapeutic use in the quantities required for this, and at justifiable production costs, and which, when used as "cellular therapeutics" give rise to no side effects—or none worth mentioning—in terms of cellular rejection and induction of tumors, particularly malignant tumors, in the patient in question.

SUMMARY OF THE INVENTION

The present invention provides a method for producing human dedifferentiated programmable stem cells using M-CSF and IL-3.

The present invention includes and provides a process for the production of dedifferentiated, programmable stem cells of human monocytic origin, comprising (a) isolating the monocytes from human blood; (b) propagating the monocytes in a culture medium, which contains cellular growth factor M-CSF; (c) simultaneously cultivating the monocytes with or subsequently to step (b) in a culture medium comprising IL-3; and (d) obtaining human adult dedifferentiated programmable stem cells by separating from culture medium.

The present invention includes and provides a process for the production of dedifferentiated, programmable stem cells of human monocytic origin, comprising (a) providing human monocytes; (b) propagating the monocytes in a culture medium, which contains cellular growth factor M-CSF; (c) simultaneously cultivating the monocytes with or subsequently to step (b) in a culture medium comprising IL-3; and (d) obtaining human adult dedifferentiated programmable stem cells by separating from culture medium.

The present invention includes and provides a dedifferentiated, programmable stem cell of human monocytic origin, wherein the cell is characterized by exhibiting a CD14 antigen and an antigen selected from the group consisting of CD90, CD117, CD123 and CD135.

The present invention includes and provides a dedifferentiated, programmable stem cell of human monocytic origin, wherein the cell is characterized by exhibiting a CD14 antigen and a CD123 antigen.

The present invention includes and provides a dedifferentiated, programmable stem cell of human monocytic origin, wherein the cell is characterized by exhibiting a CD14 antigen and a CD135 antigen.

The present invention includes and provides a dedifferentiated, programmable stem cell of human monocytic origin, wherein the cell is characterized by exhibiting a CD14 antigen, a CD123 antigen and a CD135 antigen.

The present invention includes and provides a dedifferentiated, programmable stem cell of human monocytic origin manufactured by a process comprising (a) isolating monocytes from human blood; (b) propagating monocytes in a culture medium, which contains cellular growth factor M-CSF; (c) simultaneously cultivating monocytes with or subsequently to step (b) in a culture medium comprising IL-3; and (d) obtaining human adult dedifferentiated programmable stem cells by separating from culture medium.

The present invention includes and provides a pharmaceutical composition comprising a dedifferentiated, programmable stem cell of human monocytic origin, wherein the cell is characterized by exhibiting a CD14 antigen and an antigen selected from the group consisting of CD90, CD117, CD123 and CD135.

The present invention includes and provides a pharmaceutical composition comprising a dedifferentiated, programmable stem cell of human monocytic origin, wherein the cell is characterized by exhibiting a CD14 antigen and a CD135 antigen.

The present invention includes and provides a pharmaceutical composition comprising a dedifferentiated, programmable stem cell of human monocytic origin, wherein the cell is characterized by exhibiting a CD14 antigen and a CD123 antigen.

The present invention includes and provides a pharmaceutical composition comprising a dedifferentiated, programmable stem cell of human monocytic origin, wherein the cell is characterized by exhibiting a CD14 antigen, a CD123 antigen and a CD135 antigen.

The present invention includes and provides a method of producing target cells from dedifferentiated, programmable stem cells of human monocytic origin comprising (a) obtaining desired target cells from a target tissue; (b) incubating the desired target cells in a suitable culture medium; and (c) providing supernatent from the culture medium after incubation with the desired target cells to dedifferentiated, programmable stem cells of human monocytic origin that are characterized by exhibiting a CD14 antigen and an antigen selected from the group consisting of CD90, CD117, CD123 and CD135 to differentiate said stem cells of human monocytic origin into target cells.

The present invention includes and provides a method of producing target cells from dedifferentiated, programmable stem cells of human monocytic origin comprising (a) obtaining desired target cells from a target tissue; (b) incubating the desired target cells in a suitable culture medium; and (c) providing supernatent from the culture medium after incubation with the desired target cells to dedifferentiated, programmable stem cells of human monocytic origin that are characterized by exhibiting a CD14 and a CD135 antigen to differentiate said stem cells of human monocytic origin into target cells.

The present invention includes and provides a method of producing target cells from dedifferentiated, programmable stem cells of human monocytic origin comprising (a) obtaining desired target cells from a target tissue; (b) incubating the desired target cells in a suitable culture medium; and (c) providing supernatent from the culture medium after incubation with the desired target cells to dedifferentiated, programmable stem cells of human monocytic origin that are characterized by exhibiting a CD14 antigen and a CD123 antigen to differentiate said stem cells of human monocytic origin into target cells.

The present invention includes and provides a method of producing target cells from dedifferentiated, programmable stem cells of human monocytic origin comprising (a) obtaining desired target cells from a target tissue; (b) incubating the desired target cells in a suitable culture medium; and (c) providing supernatent from the culture medium after incubation with the desired target cells to dedifferentiated, programmable stem cells of human monocytic origin that are characterized by exhibiting a CD14 antigen, a CD123 antigen and a CD135 antigen to differentiate said stem cells of human monocytic origin into target cells.

According to the present invention, the methods of producing target cells from dedifferentiated, programmable stem cells of human monocytic origin thus start with the isolation of desired target cells (step a), i.e. the isolation of differentiated cells of the cell type which is to be produced using the dedifferentiated, programmable stem cells. The differentiated target cells can be incubated in a cell culture medium (step b). Supernatent from the cell culture medium of the differentiated target cells can be used to differentiate stem cells of human monocytic origin into target cells (c).

The present invention includes and provides a dedifferentiated, programmable stem cell of human monocytic origin, wherein the cell is characterized by the membrane associated monocyte-specific surface antigen CD14 and at least one pluripotency marker selected from the group consisting of CD117, CD123 and CD135.

The present invention includes and provides a dedifferentiated, programmable stem cell preparation comprising a dedifferentiated, programmable stem cell of human monocytic origin of the present invention in a suitable medium.

The present invention includes and provides a method for treating liver cirrhosis using a pharmaceutical composition comprising dedifferentiated programmable stem cells of the present invention.

The present invention includes and provides a method of making a pharmaceutical composition for treating liver cirrhosis by preparing a composition comprising dedifferentiated programmable stem cells of the present invention.

The present invention includes and provides a method for treating pancreatic insufficiency using a pharmaceutical composition comprising dedifferentiated programmable stem cells of the present invention.

The present invention includes and provides a method of making a pharmaceutical composition for treating pancreatic insufficiency by preparing a composition comprising dedifferentiated programmable stem cells of the present invention.

The present invention includes and provides a method for treating acute or chronic kidney failure using a pharmaceutical composition comprising dedifferentiated programmable stem cells of the present invention.

The present invention includes and provides a method of making a pharmaceutical composition for treating acute or chronic kidney failure by preparing a composition comprising dedifferentiated programmable stem cells of the present invention.

The present invention includes and provides a method for treating hormonal underfunctioning using a pharmaceutical composition comprising dedifferentiated programmable stem cells of the present invention.

The present invention includes and provides a method of making a pharmaceutical composition for treating hormonal underfunctioning by preparing a composition comprising dedifferentiated programmable stem cells of the present invention.

The present invention includes and provides a method for treating cardiac infarction using a pharmaceutical composition comprising dedifferentiated programmable stem cells of the present invention.

The present invention includes and provides a method of making a pharmaceutical composition for treating cardiac infarction by preparing a composition comprising dedifferentiated programmable stem cells of the present invention.

The present invention includes and provides a method for treating pulmonary embolisms using a pharmaceutical composition comprising dedifferentiated programmable stem cells of the present invention.

The present invention includes and provides a method of making a pharmaceutical composition for treating pulmonary embolisms by preparing a composition comprising dedifferentiated programmable stem cells of the present invention.

The present invention includes and provides a method for the treatment of stroke using a pharmaceutical composition comprising dedifferentiated programmable stem cells of the present invention.

The present invention includes and provides a method of making a pharmaceutical composition for the treatment of stroke by preparing a composition comprising dedifferentiated programmable stem cells of the present invention.

The present invention includes and provides a method for the treatment of skin damage using a pharmaceutical composition comprising dedifferentiated programmable stem cells of the present invention.

The present invention includes and provides a method of making a pharmaceutical composition for the treatment of skin damage by preparing a composition comprising dedifferentiated programmable stem cells of the present invention.

The present invention includes and provides differentiated, isolated, somatic target cells and/or target tissue, characterized by the membrane-associated surface antigen CD14. Such cells can be obtained, for example, without limitation, by reprogramming the stem cells according to a method of the present invention.

The present invention includes and provides differentiated, isolated, somatic target cells and/or target tissue characterized by the membrane-associated surface antigen CD14 where the target cells and/or target tissue is selected from the group consisting of adipocytes, neurons, glia cells, endothelial cells, keratinocytes, hepatocytes and islet cells.

The present invention includes and provides differentiated, isolated, somatic target cells and/or target tissue, characterized by the membrane-associated surface antigen CD14, further comprising a transfected gene. Such cells can be obtained, for example, without limitation, by reprogramming the stem cells according to a method of the present invention.

The present invention includes and provides implantable materials coated with the dedifferentiated, programmable stem cells including differentiated, isolated, somatic target cells and/or target tissue, obtained by reprogramming the stem cells according to a method of the present invention.

The present invention includes and provides implantable materials that are prostheses, including those selected from the group consisting of cardiac valves, vessel prostheses, bone and joint prostheses, coated with the dedifferentiated, programmable stem cells including differentiated, isolated, somatic target cells and/or target tissue, obtained by reprogramming the stem cells according to a method of the present invention.

The present invention includes and provides implantable materials that are artificial and/or biological carrier materials comprising the dedifferentiated, programmable stem cells including differentiated, isolated, somatic target cells and/or target tissue, obtained by reprogramming the stem cells according to a method of the present invention.

The present invention includes and provides implantable materials that are bags or chambers for introduction into the human body containing differentiated, isolated, somatic target cells and/or target tissue, obtained by reprogramming the stem cells according to a method of the present invention.

The present invention includes and provides implantable materials that are bags or chambers, containing islet cells of the present invention, for introduction into the human body containing differentiated, isolated, somatic target cells and/or target tissue, obtained by reprogramming the stem cells according to a method of the present invention for the production of a pharmaceutical construct for use as an artificial islet cell portchamber for the supply of insulin.

The present invention includes and provides implantable materials that are bags or chambers, containing adipocytes of the present invention, for introduction into the human body containing differentiated, isolated, somatic target cells and/or target tissue, obtained by reprogramming the stem cells according to a method of the present invention for the production of a pharmaceutical construct, which contains artificial polymers filled with adipocytes, for breast construction after surgery and for use in the case of plastic and/or cosmetic correction.

The present invention includes and provides implantable materials that are semi-permeable port chamber systems comprising the dedifferentiated, programmable stem cells including differentiated, isolated, somatic target cells and/or target tissue, obtained by reprogramming the stem cells according to a method of the present invention.

The present invention includes and provides implantable materials that are semi-permeable port chamber systems comprising the dedifferentiated, programmable stem cells including differentiated, isolated, somatic target cells and/or target tissue, obtained by reprogramming the stem cells according to a method of the present invention for the production of a pharmaceutical construct for in vivo treatment of endocrine, metabolic or hemostatic diseases.

BRIEF DESCRIPTION OF THE FIGURES

FIG. 1 shows the antibody-staining of neurons and glia cells after differentiation from dedifferentiated programmable stem cells. Glia cells were stained using GFAP (left-hand picture, x200), precursor cells were stained using S100-antigen (middle picture, x200) and neurons using synaptophysin MAP2 (right-hand picture, x200).

FIG. 2 shows endothelial cells were made visible by staining with the corresponding endothelium-specific antibody CD31. Cells were incubated on Matrigel for 5 days (middle picture, development of tubular strands, x200), 8 days (right picture, formation of three-dimensional network structures, x200) and 12 days (left-hand picture, formation of vessel-like three-dimensional tube, x200).

FIG. 3 shows intermediate steps in the production of fat cells from adult stem cells. FIG. 3A shows precursor cells containing fat vacuoles. FIGS. 3B and 3C show single adipocytes stained with Sudan red. FIG. 3D shows aggregation and cluster formation of cells observed macroscopically as fat tissue. FIG. 3E shows cells of monocytic origin cultured in nutrient medium lacking IL 3 and 2-mercaptoethanol. FIG. 3F shows cells treated with nutrient medium instead of FCCM after 6 days in complete medium. FIG. 3G shows the molecular characterization, using RT-PCR, of fat cells (adipocytes) with monocytic origin through comparison of the gene expression for several genes. The specific amplificates are shown by arrows indicating their size.

FIG. 4 shows development of hepatocytes from dedifferentiated programmable stem cells of monocytic origin. Staining with anti-alpha-fetoprotein is shown after culture in the liver cell differentiation medium for 6 days in FIG. 4A; for 10 days in FIG. 4B; and for 12 days in FIG. 4C. FIG. 4D shows molecular characterization, using RT-PCR, of the hepatocytes with monocytic origin through comparison of the gene expression for several genes. The specific amplificates are shown by arrows indicating their size.

FIG. 5 shows development of keratinocytes from the dedifferentiated programmable stem cells of monocytic origin. Staining of cytokeratin 5 and 6 is shown after culture in the keratinocyte differentiation medium for 6 days in FIG. 5A and for 10 days in FIG. 5B.

FIG. 6 shows immunohistochemical phenotyping of the cell population of dedifferentiated programmable stem cells of monocytic origin on cytospin preparations which had more than 70% vital cells with typical stem cell morphology.

FIG. 7 shows in vivo differentiation of dedifferentiated programmable stem cells of monocytic origin in rats by detection of stem cells from punch biopsies. FIG. 7A shows FISH Y-chromosome detection in stem cell derived hepatocytes after 5 days. FIG. 7B shows FISH Y-chromosome detection in stem cells derived hepatocytes, endothelial cells, and bile duct epithelial cells after 25 days.

FIG. 8 shows the insulin content of the supernatant from cultures of insulin-producing cells derived from programmable stem cells of monocytic origin measured by means of ELISA for human insulin.

FIG. 9 shows the albumin content of the supernatant from cultures of hepatocytes derived from programmable stem cells of monocytic origin measured by means of ELISA for human albumin.

FIG. 10 shows double-staining of the phenotypic marker for monocytes, CD14, and the liver-specific marker, albumin, to determine expression of the monocyte-specific antigen, CD14, and albumin in hepatocytes derived from dedifferentiated stem cells.

FIG. 11 shows the results of FACS-Analysis using a FITC-marked anti-CD14 antibody or a FITC-marked anti-albumin antibody to determine expression of the monocyte-specific antigen, CD14, and the liver-specific marker, albumin, in hepatocytes derived from dedifferentiated stem cells.

DETAILED DESCRIPTION

Figure 7C:
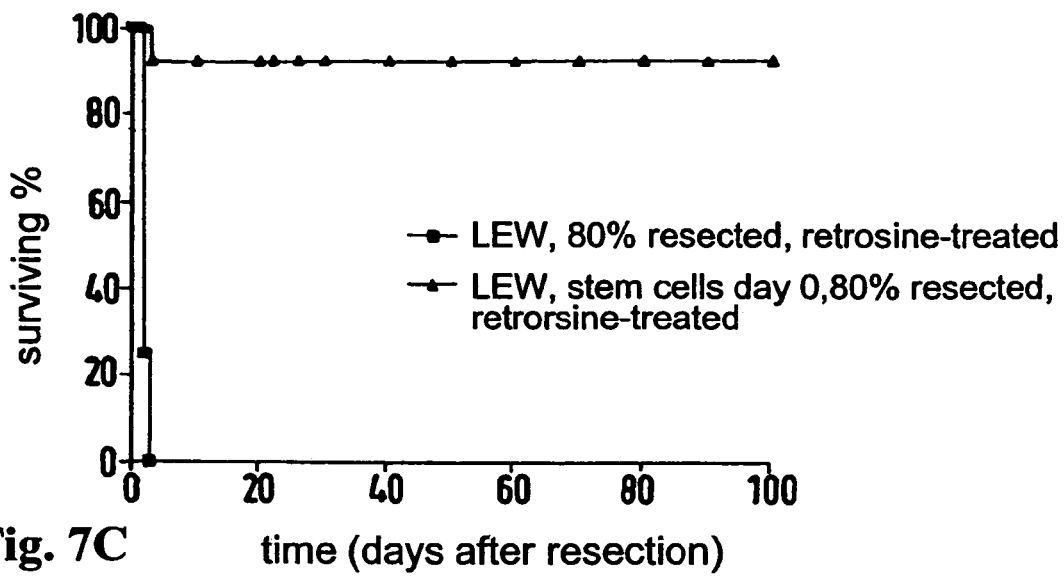
FIG. 7C shows Kaplan-Meier survival curves of stem-cell treated versus untreated recipient rats following administration of retrorsine and 80% liver resection.

The invention relates to adult dedifferentiated programmable stem cells derived from human monocytes, as well as their production and use for the production of body cells and tissues. According to a particularly preferred embodiment of the invention these cells are autologous human stem cells, i.e., the cell of monocytic origin comes from the patient who is to be treated with the stem cell produced from the original cell and/or with the body cells produced from this stem cell.

According to the invention this problem is solved by the production of dedifferentiated programmable cells from human monocytes which, for the purposes of the invention, are referred to hereafter as "stem cells". The term "dedifferentiation" is familiar to the person skilled in the relevant art, cf. for Weissman I. L., Cell 100: 157-168, FIG. 4, (2000). It signifies the regression of an adult, already specialized (differentiated) body cell to the status of a stem cell, i.e., of a cell, which in turn can be transferred (programmed) into a number of cell types. Surprisingly, it has been demonstrated that the process according to the invention leads to the dedifferentiation of monocytes. The stem cells produced in this way can be transformed (programmed) into a large number of different target cells/target tissue, cf. examples. The stem cells according to the invention express, in addition to the CD14 surface antigen characteristic of differentiated monocytes, at least one, preferably two or three, of the typical pluripotency markers CD90, CD117, CD123 and CD135. In a particularly preferred manner, the stem cells produced according to the invention express the CD14 surface antigen as well as the four pluripotency markers CD90, CD117, CD123 and CD135, cf. Example 2, Table 1. Preferably, the stem cells of the invention express the membrane associated monocyte-specific surface antigen CD14 and at least one pluripotency markers selected from the group consisting of CD117, CD123 and CD135. More preferably, the stem cells of the invention carry the CD14 antigen in combination with at least the pluripotency marker CD123 and/or CD135. Less than 3%, preferably less than 1% of the stem cells according to the invention express the CD34 antigen. Most preferably, none of the stem cells of the invention express the CD34 antigen. In this way, for the first time adult stem cells are made available, which can within a short time be reprogrammed into preferably autologous tissues.

The generation of the stem cells according to the invention is completely harmless to the patient and—in the case of autologous use—comparable to own blood donation. The quantity of stem cells ($10^8$ to $10^9$ cells) required for the usual therapy options (see above) can be made available cost-effectively within 10 to 14 days after the blood is taken. In addition the cell product provided for the therapy, in the case of autologous use, does not give rise to any immunological problem in terms of cell rejection, as cells and recipient are preferably genetically identical.

The stem cells according to the invention have also proved to be risk-free in animal experimentation and in culture with regard to giving rise to malignancy, a result which is only to be expected due to the cell of monocytic origin, from which the stem cells according to the invention derive.

In one aspect, steps of the process according to the invention for the production of dedifferentiated programmable stem cells of human monocytic origin comprise:

(a) Isolation of monocytes from human blood;

(b) Propagating the monocytes in a suitable culture vessel containing cell culture medium, which contains the macrophage-colony-stimulating factor (hereafter referred to as M-CSF); and (c) Cultivating the monocytes in the presence of interleukin-3 (IL-3); and (d) Obtaining the human dedifferentiated programmable stem cells, by separating the cells from the culture medium.

According to a particularly preferred embodiment of the process, M-CSF and IL-3 are simultaneously added to the cell culture medium in Step b).

It is however also possible, initially only to add M-CSF to the cell culture medium in Step b) in order to cause the monocytes to propagate, and to add IL-3 to the cell culture medium subsequently.

Finally the process in Step b) can also be carried out in such a way that the monocytes are initially propagated in a cell culture medium containing only M-CSF, then the medium is separated from the cells and a second cell culture medium is then used, which contains IL-3.

According to a preferred embodiment of the invention the culture medium of Step b) is separated from the cells attached to the bottom of the culture vessel and the human, dedifferentiated, programmable stem cells are obtained by detaching the cells from the bottom and by isolating the cells.

According to a preferred embodiment of the invention the cells are further cultivated in the presence of a sulfur compound. The cultivation can be carried out in a separate process step which follows the cultivation Step b) illustrated above. It can however also be carried out in Step b), by further adding the sulfur compound to the culture medium, preferably already at the start of the cultivation.

The process according to the invention surprisingly leads to the dedifferentiation of the monocytes, wherein the adult stem cells resulting from the dedifferentiation, besides the CD14 surface antigen typical of the differentiated monocytes, also express at least one or more, preferably all of the pluripotency markers CD90, CD117, CD123 and CD135 (cf. Table 1). Preferably, the stem cells of the invention express the membrane associated monocyte-specific surface antigen CD14 and at least one pluripotency markers selected from the group consisting of CD117, CD123 and CD135. More preferably, the stem cells of the invention carry the CD14 antigen in combination with at least the pluripotency marker CD123 and/or CD135. Less than 3%, preferably less than 1% of the stem cells according to the invention express the CD34 antigen. Most preferably, none of the stem cells of the invention express the CD34 antigen. The expression of the respective markers (surface antigens) can be proved by means of commercially available antibodies with specificity against the respective antigens to be detected, using standard immuno assay procedures, cf. Example 2.

As the cells, during the propagation and dedifferentiation process, adhere to the bottom of the respective culture vessel, it is necessary to separate the cells from the culture medium from Step b) and to detach them from the bottom after completion of the dedifferentiation. According to a preferred embodiment of the invention the cell culture supernatant is discarded before the detaching of the cells adhering to the bottom and subsequently, the adhering cells are preferably rinsed with fresh culture medium. Following the rinsing, fresh culture medium is again added to the cells adhering to the bottom, and the step of releasing the cells from the bottom then follows (cf. Example 13).

According to a preferred embodiment the cells are brought into contact with a biologically well-tolerated organic solvent, at the end of Step c) and before Step d). A biologically well-tolerated organic solvent can be an alcohol with 1-4 carbon atoms, the use of ethanol being preferred.

In a further embodiment, at the end of Step c) and before Step d) the cells are brought into contact with the vapor phase of the biologically well-tolerated organic solvent.

The detaching can moreover also be carried out mechanically, however, an enzymatic detaching process is preferred, for example with trypsin.

The dedifferentiated programmable stem cells obtained in this way, floating freely in the medium, can either be directly transferred to a reprogramming process, or kept in the culture medium for a few days; in the latter case, a cytokine or LIF (leukemia inhibitory factor) is preferably added to the medium, in order to avoid premature loss of the programmability (cf Donovan, P. J., Gearhart, J., loc. cit., Page 94). Finally the cells can be deep-frozen for storage purposes without loss of programmability.

The stem cells according to the invention differ from the pluripotent stem cells of embryonic origin known hitherto and from the known adult stem cells from different tissues, in that besides the membrane-associated monocyte-specific CD14 surface antigen, they carry at least one pluripotency marker from the group consisting of CD90, CD117, CD123 and CD135 on their surface. Preferably, the stem cells of the invention carry the membrane associated monocyte-specific surface antigen CD14 and at least one pluripotency markers selected from the group consisting of CD117, CD123 and CD135. More preferably, the stem cells of the invention carry the CD14 antigen in combination with at least the pluripotency marker CD123 and/or CD135. Less than 3%, preferably less than 1% of the stem cells according to the invention express the CD34 antigen. Most preferably, none of the stem cells of the invention express the CD34 antigen.

The stem cells produced using the process according to the invention can be reprogrammed into any body cells. Processes for reprogramming stem cells are known in the state of the art, cf. for example Weissman I. L., Science 287: 1442-1446 (2000) and Insight Review Articles Nature 414: 92-131 (2001), and the handbook "Methods of Tissue Engineering", Eds. Atala, A., Lanza, R. P., Academic Press, ISBN 0-12-436636-8; Library of Congress Catalog Card No. 200188747.

The differentiated isolated somatic target cells and/or the target tissue obtained by reprogramming of the stem cells according to the invention moreover carry the membrane-associated CD14 differentiation marker of the monocytes. Additionally, less than 3%, preferably less than 1% of these somatic target cells and/or these target tissues according to the invention express the CD34 antigen. Most preferably, none of these cells or tissues express the CD34 antigen. As shown in Example 11, hepatocytes which are derived from the stem cells according to the invention, express the CD14 surface marker which is typical of monocytes, while at the same time they produce the protein albumin, which is typical of hepatocytes. The hepatocytes derived from the stem cells according to the invention can therefore be distinguished from natural hepatocytes. In the same way, the membrane-associated CD14 surface marker was detected on insulin-producing cells, which were derived from the stem cells according to the invention (Example 9).

In one embodiment of the invention the dedifferentiated, programmable stem cells are used for the in-vitro production of target cells and target tissue (cf. Examples). Accordingly the invention provides methods of producing target cells from dedifferentiated, programmable stem cells of human monocytic origin which methods comprise the isolation of desired target cells as a first step (a), i.e. the isolation of differentiated cells of the cell type which is to be produced using the dedifferentiated, programmable stem cells. The differentiated desired target cells can be incubated in a cell culture medium (as a second step, b). Supernatent from the cell culture medium of the differentiated target cells can be used to differentiate stem cells of human monocytic origin into target cells (in a third step, c). Illustrated methods are set forth in further detail in Example 6 (adipocytes), Example 7 (hepatocytes) and Example 8 (keratinocytes). Therefore, differentiated, isolated tissue cells, which are obtained by differentiation (reprogramming) of the stem cells according to the invention, and which carry the membrane-associated CD14 surface antigen, are also subject of the present invention.

The stem cells according to the invention are preferably simply and reliably differentiated in vitro into desired target cells, such as for example adipocytes (cf. Example 6), neurons and glia cells (cf. Example 3), endothelial cells (cf. Example 5), keratinocytes (cf Example 8), hepatocytes (cf. Example 7) and islet cells (islet of Langerhans, cf. Example 9), by growing the stem cells in a medium which contains the supernatant of the culture medium, in which the respective target cells and/or fragments thereof have been incubated (cf. Examples 6 to 8). This supernatant is referred to hereafter as "target-cell-conditioned medium".

For the differentiation (reprogramming) of the dedifferentiated stem cells according to the invention the following procedure can therefore be followed, in which:

a) tissue which contains or consists of the desired cells is crushed;
b) the desired tissue cells and/or fragments of these are obtained;
c) the desired cells and/or fragments of these are incubated in a suitable culture medium;
d) the culture medium supernatant is collected during and after the incubation as desired-cell-conditioned medium; and
e) for the reprogramming/differentiation of dedifferentiated stem cells into the desired cells or tissue, the stem cells are grown in the presence of the desired-cell-conditioned medium.

Standard cell culture media can be used as culture medium (cf. Examples). The media preferably contain growth factors, such as for example the epidermal growth factor.

The incubation of the desired cells and/or fragments of these ("cell pellet") can be carried out over 5 to 15, preferably 10 days. The supernatant, i.e., the desired-cell-conditioned medium is preferably removed in each case after 2 to 4 days and replaced by fresh medium. The supernatants thus obtained can be filtered under sterile conditions separately or pooled and stored at approximately −20° C. or used directly for the programming of stem cells. As shown above, the programming of the stem cells into the desired target cells is carried out by growing stem cells in the presence of the medium conditioned with the respective desired cells (cf Examples). The growth medium preferably additionally contains a desired-cell-specific growth factor, such as for example the "hepatocyte growth factor" or the "keratinocyte growth factor" (cf. Examples).

In one embodiment of the invention the dedifferentiated, programmable stem cells according to the invention are used per se for the production of a pharmaceutical composition for the in-vivo production of target cells and target tissue.

Such pharmaceutical preparations can contain the stem cells according to the invention suspended in a physiologically well-tolerated medium. Suitable media are for example PBS (phosphate buffered saline) or physiological saline with 20% human albumin solution and the like.

These pharmaceutical preparations contain vital dedifferentiated, programmable stem cells according to the invention, which have on their surface the CD14 surface marker and at least one more of the multipotent stem cell markers CD90, CD117, CD123 and/or CD135, in a quantity of at least 1, 2, 3, 4, 5, 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50%, preferably 60 or 70%, particularly preferably 80 or 90% and extremely preferably 100%, relative to the total number of the cells present in the preparation, and optionally further pharmaceutically well-tolerated adjuvants and/or carrier substances.

Stem cell preparations can contain vital dedifferentiated, programmable stem cells according to the invention, which have on their surface the CD14 surface marker and at least one more of the pluripotent stem cell markers CD90, CD117, CD123 and/or CD135, in a quantity of at least 1, 2, 3, 4, 5, 6, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58 or 59%, preferably at least 60%, relative to the total number of the cells present in the preparation; cell suspensions in a cell culture- or transport medium well-tolerated by cells, such as e.g., PBS or RPMI etc., or deep-frozen cell preparations in a suitable storage medium, such as e.g., RPMI with 50% human albumin solution and 10% DMSO are preferred.

The number of vital cells and hence the proportion of these in the compositions referred to above, can be determined optically by use of the "Trypan blue dye exclusion technique", as vital cells can be optically distinguished from non-vital cells, using this dye.

As a rule, it will be irrelevant for clinical use, if some of the cells present in the pharmaceutical preparation do not fulfil the criteria of dedifferentiated, programmable stem cells according to the invention, provided that a sufficient number of functional stem cells is present. It is however also possible to eliminate non-dedifferentiated cells by means of processes known in the state of the art on the basis of surface markers typical of the dedifferentiated cells according to the invention in such preparations, so that these contain the desired cells in essentially pure form. One example of a suitable process is "Immuno magnetic bead sorting", cf. Romani et al., J. Immunol. Methods 196: 137-151 (1996).

Stem cells further have the capability, of spontaneously differentiating in vivo by direct contact with a cell group of a specific cell type into cells of this type. Processes for tissue production using cells which can be redifferentiated ("tissue engineering") are known in the state of the art. For example Wang, X. et al. ("Liver repopulation and correction of metabolic liver disease by transplanted adult mouse pancreatic cells" Am. J. Pathol. 158 (2): 571-579 (2001)), have shown that even certain adult cells of the pancreas in mice are able to transform, in FAH-(fumaroylacetoacetate hydrolase)-deficient mice, into hepatocytes, which can fully compensate for the metabolic defect in these animals. A further example is the experiments of Lagasse et al., "Purified hematopoietic stem cells can differentiate into hepatocytes in vivo", Nature Medicine, 6 (11): 1229-1234 (2000). The authors have shown that hematopoietic stem cells from bone marrow were able, after in-vivo transfer into FAH-deficient mice, to transform into hepatocytes, which could then compensate for the metabolic defect; see also the review by Grompe M., "Therapeutic Liver Repopulation for the Treatment of Metabolic Liver Diseases" Hum. Cell, 12: 171-180 (1999).

Particularly preferable forms of application for the in-vivo differentiation of the dedifferentiated stem cells according to the invention are injection, infusion or implantation of the stem cells into one specific cell association in the body, in order to allow for the stem cells to differentiate there, by direct contact with the cell association, into cells of this cell type. For injection or infusion the cells can be administered in PBS (phosphate buffered saline).

Preferred examples of the relevant indications in this connection are: cirrhosis of the liver, pancreatic insufficiency, acute or chronic kidney failure, hormonal under-functioning, cardiac infarction, pulmonary embolism, stroke and skin damage.

Therefore preferred embodiments of the invention are the use of the dedifferentiated, programmable stem cells for the production of different pharmaceutical compositions for the treatment of cirrhosis of the liver, pancreatic insufficiency, acute or chronic kidney failure, hormonal under-functioning, cardiac infarction, pulmonary embolism, stroke and skin damage.

For the therapeutic use of the target cells obtainable from the stem cells according to the invention, a number of concepts are available (see above Science 287: 1442-1446 (2000) and Nature 414: 92-131 (2001)).

A further preferred application concerns the injection of the dedifferentiated stem cells according to the invention into the peritoneum, so that they differentiate there, due to the influence of the cells surrounding them, into peritoneal cells. In the case of peritoneal dialysis of patients with kidney insufficiency, these cells can take over a kidney function via their semi-permeable membrane and give off kidney dependent waste substances into the peritoneum from where these are removed via the dialysate.

Therefore, also the differentiated, isolated, somatic target cells and/or target tissue, which are obtained by reprogramming of the stem cells and are characterized by the membrane-associated CD14 antigen are subject of the invention. These somatic target cells and/or target tissue preferably contain adipocytes, neurons and glia cells, endothelial cells, keratinocytes, hepatocytes and islet cells.

However the cells can also be introduced directly into the organ to be reconstituted. The introduction can be carried out via matrix constructions which are coated with corresponding differentiated cells or cells capable of differentiation. The matrix constructions are as a rule biodegradable, so that they disappear out of the body while the newly introduced cells grow together with the cells present. From this point of view, for example cellular, preferably autologous transplants in the form of islet cells, hepatocytes, fat cells, skin cells, muscles, cardiac muscles, nerves, bones, endocrine cells etc. come under consideration for restitution for example after partial surgical resection of an organ, for repair for example after trauma or for supportive use, for example in the case of lacking or insufficient organ function.

The stem cells according to the invention and target cells obtained from them can further be used to coat implantable materials, in order to increase biocompatibility. Therefore, also implantable materials, which are coated with the dedifferentiated, programmable stem cells or the somatic target cells and/or target tissue are subject of the invention. According to one embodiment of the invention these implantable materials are prostheses. In particularly preferred embodiments these prostheses are cardiac valves, vessel prostheses, bone- and joint prostheses.

The implantable materials can also be artificial and/or biological carrier materials, which contain the de-differentiated, programmable stem cells or target cells. In this regard, the carrier materials can be bags or chambers for insertion into the human body.

In one embodiment of the invention such a bag, containing islet cells, which are differentiated somatic cells according to the invention, is used for the production of a pharmaceutical construct for use as an artificial islet cell port chamber for the supply of insulin.

According to a further embodiment of the invention, a bag or chamber containing adipocytes, which are differentiated somatic cells according to the invention, is used for the production of an artificial polymer filled with adipocytes as a pharmaceutical construct for breast construction after surgery and in the case of further indications of plastic and/or cosmetic correction.

Moreover, semi-permeable port chamber systems, containing endocrine cells of very widely varying provenance, can be used in vivo for the treatment of endocrine, metabolic or hemostatic disorders. Examples of such endocrine cells are cells which produce thyroxine, steroids, ADH, aldosterone, melatonin, serotonin, adrenalin, noradrenalin, TSH, LH, FSH, leptin, cholecystokinin, gastrin, insulin, glucagon, or clotting factors.

Therefore, also implantable materials, which are semi-permeable port chamber systems, containing differentiated isolated somatic target cells are subject of the invention. These semi-permeable chamber systems are used in different embodiments of the invention for the production of a pharmaceutical construct for the in-vivo treatment of endocrine, metabolic or hemostatic disorders.

The target cells obtained from the stem cells according to the invention can in addition be used as cell cultures in bioreactors outside the body, for example in order to carry out detoxification reactions. This form of use is particularly relevant in the case of acute conditions, for example in the case of acute liver failure as a hepatocyte-bioreactor.

The production of the constructs illustrated above and conducting the corresponding therapeutic process have already been illustrated many times in the state of the art, compare for example the review by Lalan, S., et al. "Tissue engineering and its potential impact on surgery" World J. Surg. 25: 1458-1466 (2001); Nasseri, B. A., et al. "Tissue engineering: an evolving 21st-century science to provide replacement for reconstruction and transplantation" Surgery 130: 781-784 (2001) and Fuchs, J. R., et al., "Tissue engineering: a 21st century solution to surgical reconstruction" Ann. Thorac. Surg. 72: 577-591 (2001).

Finally, the pluripotent stem cells according to the invention open up a broad field for transgenic modification and therapy. According to a preferred embodiment of the invention the dedifferentiated programmable stem cells per se or somatic target cells and/or target tissue finally differentiated from these, are transfected with one or more genes. In this way, one or more genes which are required to maintain the metabolism of certain organs, such as for example livers or kidneys, are restored and/or supported or reintroduced. For example, stem cells or hepatocytes derived from these can be transfected with the FAH (fumaroylacetoacetate hydrolase) gene. In the FAH-deficient mouse model the intrasplenic injection of 1000 FAH-positive donor hepatocytes was sufficient to completely repopularize the liver after 6 to 8 weeks and fully compensate for the metabolic defect leading to cirrhosis of the liver (cf. Grompe, M., et al., Nat. Genet. 12: 266 ff. (1996)).

Correspondingly, by transfection of the stem cells or the respective target cells obtained from the stem cells by programming (for example hematopoietic cells, hepatocytes, ovary cells, muscle cells, nerve cells, neurons, glia cells, cartilage or bones cells, etc.) with "Multi-Drug-Resistance-genes" extended radical chemotherapy can be made possible in the case of malignant diseases by corresponding hematopoietic reconstitution or radiation resistance can be produced.

A starting material for the process according to the invention is monocytes from human blood. These are preferably autologous monocytes, i.e., monocytes, which originate from the blood of the patient to be treated with the stem cells according to the invention or the target cells produced from these.

To obtain the monocytes the blood can first, after standard treatment with an anticoagulant in a known manner, preferably by centrifugation, be separated into plasma and into white and red blood cells. After the centrifugation the plasma is to be found in the supernatant; below this lies a layer which contains the totality of the white blood cells. This layer is also referred to as "buffy coat". Below this lies the phase containing red blood cells (hematocrit).

The "buffy coat" layer is then isolated and separated to obtain the monocytes for example by centrifuging using a known process. According to a preferred process variant the "buffy coat" layer is coated onto a lymphocyte separation medium (e.g., Ficoll Hypaque) and centrifuged. By further centrifuging and rinsing, the monocyte fraction is obtained from the blood (cf. Example 1).

Examples of alternative processes for obtaining the monocytes from complete blood are "Fluorescence-Activated Cell Sorting" (FACS), "Immunomagnetic Bead Sorting" (cf. Romani et al., J. Immunol. Methods 196: 137-151 (1996)) and "Magnetic-Activated Cell Sorting" (MACS) or the so called "Rosetting process" (cf. Gmelig-Meyling, F., et al., "Simplified procedure for the separation of human T and non-T cells" Vox Sang. 33: 5-8 (1977)).

According to the invention, monocytes can be obtained from any isolated human blood, and the blood can also originate from organs such as the spleen, lymph nodes or bone marrow. Obtaining monocytes from organs is considered especially when the separation of the monocytes from human blood, e.g., in the case of anemia or leukemia, is not possible, or not in sufficient quantities, and in the case of allogenic use, if, within the framework of multi-organ removal, the spleen is available as a source for isolation of monocytes.

For the production of a sufficient quantity of stem cells according to the invention it is first necessary to propagate the monocytes. For this purpose, growth media suitable for monocytes can be used, wherein, according to the invention said medium contains M-CSF (macrophage colony stimulating factor). M-CSF (also referred to as CSF-1) is produced by monocytes, fibroblasts and endothelial cells. The concentration of M-CSF in the culture medium can amount to 2 to 20 µg/l medium, preferably 4 to 6 µg/l and in a particularly preferred manner 5 µg/l.

On the monocytes M-CSF binds to the specific c-Fms receptor (also referred to as CSF-1R), which is exclusively present on the surface of monocytes and which only binds M-CSF (Sherr C. J., et al., Cell 41 (3): 665-676 (1985)). As the specific interaction between M-CSF and the receptor induces the division of the monocytes, the medium, in which the monocytes are cultivated contains M-CSF or an analogue thereof, which can bind to the receptor and activate it. Other growth factors such as GM-CSF (granulocyte-monocyte colony stimulating factor) and G-CSF (granulocyte colony stimulating factor) are unsuitable, as, due to the lack of affinity to the c-Fms receptor, they are not capable of inducing monocyte division.

In a particularly preferred embodiment of the process M-CSF and IL-3 are simultaneously added to the cell culture medium in Step b) of the process. The concentration of IL-3 in the medium may amount to 0.2 to 1 µg/l, preferably 0.3 to 0.5 µg/l and in a particularly preferred manner 0.4 µg IL-3/l.

It is however also possible, to add initially only M-CSF to the cell culture medium in Step b) and add IL-3 only thereafter.

In a further embodiment the culture vessel initially contains cell culture medium which contains only M-CSF, which after the separation of the cells is then replaced by a second cell culture medium, which contains IL-3.

According to a preferred embodiment of the invention the cells in Step b) of the process are additionally cultivated in the presence of a sulfur compound, e.g., a mercapto compound, in which at least one hydrocarbon group is bonded to the sulfur, and said hydrocarbon group(s) may be substituted with one or more functional groups. Mercapto compounds are defined as compounds which have at least one mercapto group (—SH), which is bonded to a hydrocarbon group. By the additional use of such a sulfur compound, the number of the stem cells obtained by dedifferentiation of the cells of monocytic origin, which express one or more of the stem cell markers CD90, CD117, CD123 and CD135, can be increased.

The functional group(s) is/are preferably hydroxyl- and/or amine groups. In a particularly preferred embodiment, the sulfur compound is 2-mercaptoethanol. According to a further preferred embodiment the sulfur compound is dimethylsulfoxide (DMSO).

The quantity of the sulfur compound used can range from approximately 4 to approximately 200 µmol/l relative to the sulfur. Approximately 100 µmol/l is preferred.

When 2-mercaptoethanol is used, the culture medium should contain approximately 3 µl to approximately 13 µl, preferably approximately 7 µl 2-mercaptoethanol/l.

The treatment with IL-3 and optionally with the sulfur compound can be carried out simultaneously with or following the propagation of the monocytes by cultivation with M-CSF, simultaneous propagation and treatment with IL-3 and optionally a sulfur compound being preferred. Propagation and dedifferentiation should, taken together, last no more than 10 days, and the treatment with IL-3 and optionally with the sulfur compound should be carried out over at least 3 and at most 10 days, preferably 6 days.

Therefore, according to the invention, in the case of cultivation of the monocytes in a culture medium, which simultaneously contains M-CSF, IL-3 and preferably a mercapto compound, the duration of cultivation until the detaching of the cells from the bottom of the culture vessel amounts to at least 3 and at most 10 days, preferably 5 to 8 days and particularly preferably 6 days.

If in a preferred embodiment the process according to the invention is carried out in such a way that the monocytes in Step b) are initially propagated in a medium containing only M-CSF, the propagation in such a culture medium can take place over a period of at least 2, preferably 3 and particularly preferably 4 days with a maximum duration of 7 days, and a subsequent cultivation in the presence of IL-3 and optionally of a mercapto compound can take place over a further 3 days. Preferably in such a case the cultivation in a medium containing only M-CSF will however only last a maximum of 4 days, followed by a cultivation in the presence of IL-3 and optionally of a mercapto compound over a period of 3, 4, 5 or 6 days.

To carry out the propagation and dedifferentiation jointly, as illustrated in Examples 2 and 13, the monocytes are after isolation transferred into a medium, which contains both M-CSF, and IL-3 as well as preferably the sulfur compound, in particular mercaptoethanol or DMSO.

Due to their adhesive properties the monocytes and the stem cells produced from them during the process adhere to the bottom of the respective culture vessel. According to a preferred embodiment of the invention, the culture medium is after Step c) separated from the cells adhering to the bottom of the culture vessel and is discarded. This is preferably followed by rinsing of the cells adhering to the bottom with culture medium, and the cells are then covered with fresh culture medium (cf. Example 13).

In this step the propagation and dedifferentiation medium illustrated above can be used as culture medium, as well as a standard cell culture medium, for example RPMI.

According to a further preferred embodiment of the invention, the cells are brought into contact with a biologically well-tolerated organic solvent at the end of Step c) and before Step d), in order to increase the number of stem cells floating freely in the medium at the end of the process. The quantity of the solvent can range from 10 µl to 1 ml. This is preferably an alcohol with 1-4 carbon atoms, the addition of ethanol being particularly preferred. According to a particularly preferred embodiment the cells are brought into contact with the vapor phase of the previously defined biologically well-tolerated organic solvent, preferably with ethanol vapor (cf Example 2). The time for exposure to the organic solvent, particularly preferably to ethanol vapor, should amount to 4-12 hours, preferably 8-10 hours.

The process according to the invention is preferably carried out in culture vessels, the surface of which has previously been coated with fetal calf serum (FCS) (cf. Example 2). Alternatively human AB-Serum from male donors can be also be used. The coating with FCS can be carried out by covering the surface of culture vessels with FCS before use, and after an exposure time of a few, in particular 2 to 12 hours, and in a particularly preferable manner 7 hours, and by removing the FCS not adhering to the surface in a suitable manner.

If treatment with organic solvent take place after Step c) optionally after exchange of the culture medium, the cells already become detached from the bottom to a certain extent in this process step. The (further) detaching can be carried out mechanically, for example with a fine cell scraper, spatula or tip of a pipette (cf. Example 13).

According to a preferred embodiment of the process, complete detaching is carried out by treatment with a suitable enzyme, for example with trypsin (cf. Example 2). The cells may be exposed to the trypsin solution (0.1 to 0.025 g/l, preferably 0.05 g/l) for 2-10 minutes at 35° C. to 39° C., preferably at 37° C., in the presence of $CO_2$.

The trypsin activity is then blocked by a standard method, and the now freely floating dedifferentiated programmable stem cells can be obtained by a standard method, for example by centrifuging and in one embodiment by suspended in a suitable cell culture at the end of Step d). They are now available, suspended in a suitable medium, for example in RPMI 1640 or DMEM, for immediate differentiation into the desired target cells. They can however also be stored in the medium for a few days. In a preferred embodiment the medium contains a cytokine or LIF factor (leukemia inhibitory factor), cf. Nature 414: 94 (2001, Donovan, P. J., Gearhardt, J., loc. cit.), if the cells are to be stored in culture for longer than approximately 48 hours as dedifferentiated programmable stem cells. In a medium containing such factors stem cells can be kept for at least 10 days as dedifferentiated programmable stem cells.

In a preferred embodiment the cells are suspended for longer storage in a liquid medium and then deep-frozen. Protocols for the deep freezing of living cells are known in the state of the art, cf. Griffith M., et al. "Epithelial Cell Culture, Cornea, in Methods of Tissue Engineering", Atala A., Lanza R. P., Academic Press 2002, Chapter 4, Pages 131 to 140. A preferred suspension medium for the deep freezing of the stem cells according to the invention is FCS-containing DMEM, cf. Example 2.

The invention is further exemplified and illustrated below with reference to examples.

If not defined within the examples, the composition of the media and substances used are as follows:

1. Penicillin/streptomycin solution:

10,000 units of penicillin as sodium salt of penicillin G and 1000 µg streptomycin as streptomycin sulfate per ml physiological sodium chloride solution (NaCl 0.9%).

2. Trypsin-EDTA 0.5 g trypsin and 0.2 g EDTA (4 Na)/l

3. Insulin human, recombinant, produced in *E. coli*, approximately 28 units/mg

4. RPMI 1640 (1×, liquid (11875)) contains L-Glutamine

RPMI (Roswell Park Memorial Institute) Media 1640 are enriched formulations, which can be used extensively for mammalian cells.

| Components | Mol.-weight | Conc. (mg/l) | Molarity (nM) |
|---|---|---|---|
| Anorganic salts | | | |
| Calcium nitrate ($Ca(NO_3)_2 4H_2O$) | 236 | 100.00 | 0.424 |
| Potassium chloride (KCl) | 75 | 400.00 | 5.30 |
| Magnesium sulfate ($MgSO_4$) | 120 | 48.84 | 0.407 |
| Sodium chloride (NaCl) | 58 | 6000.00 | 103.44 |
| Sodium bicarbonate ($NaHCO_3$) | 84 | 2000.00 | 23.800 |
| Sodium phosphate ($Na_2HPO_4$) | 142 | 800.00 | 5.63 |
| Further components | | | |
| Glucose | 180 | 2000.00 | 11.10 |
| Glutathione, reduced | 307 | 1.50 | 0.0032 |
| Phenol red | 398 | 5.00 | 0.0125 |
| Amino acids | | | |
| L-Arginine | 174 | 200.00 | 1.10 |
| L-Asparagine | 132 | 50.00 | 0.379 |
| L-Asparaginic acid | 133 | 20.00 | 0.150 |
| L-Cysteine dihydrochloride | 313 | 65.00 | 0.206 |
| L-Glutaminic acid | 147 | 20.00 | 0.136 |
| L-Glutamine | 146 | 300.00 | 2.05 |
| Glycine | 75 | 10.00 | 0.133 |
| L-Histidine | 155 | 15.00 | 0.0967 |
| L-Hydroxyproline | 131 | 20.00 | 0.153 |
| L-Isoleucine | 131 | 50.00 | 0.382 |
| L-Leucine | 131 | 50.00 | 0.382 |
| L-Lysine hydrochloride | 146 | 40.00 | 0.219 |
| L-Methionine | 149 | 15.00 | 0.101 |
| L-Phenylalanine | 165 | 15.00 | 0.0909 |
| L-Proline | 115 | 20.00 | 0.174 |
| L-Serine | 105 | 30.00 | 0.286 |
| L-Threonine | 119 | 20.00 | 0.168 |
| L-Tryptophan | 204 | 5.00 | 0.0245 |
| L-Tyrosine disodium, dihydrate | 261 | 29.00 | 0.110 |
| L-Valine | 117 | 20.00 | 0.171 |
| Vitamins | | | |
| Biotin | 244 | 0.20 | 0.008 |
| D-calcium pantothenate | 477 | 0.25 | 0.0005 |
| Choline chloride | 140 | 3.00 | 0.0214 |
| Folic acid | 441 | 1.00 | 0.0022 |
| i-Inositol | 180 | 35.00 | 0.194 |
| Niacinamide | 122 | 1.00 | 0.0081 |
| p-aminobenzoic acid (PABA) | 137 | 1.00 | 0.0072 |
| Pyridoxine HCl | 206 | 1.00 | 0.0048 |
| Riboflavin | 376 | 0.20 | 0.0005 |
| Thiamin HCl | 337 | 1.00 | 0.0029 |
| Vitamin B12 | 1355 | 0.005 | 0.00000369 |

Reference: Moore G. E., et al., J.A.M.A. 199: 519 (1967)

5. PBS (Dulbecco's phosphate buffered saline) cf. J. Exp. Med. 98:167 (1954):

| Components | g/l |
|---|---|
| KCl | 0.2 |
| $KH_2PO_4$ | 0.2 |
| NaCl | 8.00 |
| $Na_2PHO_4$ | 1.15 |

6. 2-Mercaptoethanol

Quality for synthesis; Content>98%, Density 1.115 to 1.116, cf. e.g., Momo J., et al., J. Am. Chem. Soc. 73: 4961 (1951).

7. Ficoll-Hypaque:

Lymphocyte separation medium (saccharose/epichlorohydrin-copolymerizate Mg 400,000; Density 1.077, adjusted with Sodium diatrizoate).

8. Retinic acid:

Vitamin A acid ($C_{20}H_{28}O_2$), 300 µl in 1.5 ml PBS corresponding to 1 mM. As medium for programming of neurons and glia cells use 150 µl on 10 ml medium (corresponding to $10^{-6}$ M).

9. DMEM

Dulbecco's modified Eagle medium (high glucose) cf. Dulbecco, R. et al., Virology 8: 396 (1959); Smith, J. D. et al., Virology 12: 158 (1960); Tissue Culture Standards Committee, In Vitro 6: 2 (1993)

10. L-Glutamine

Liquid: 29.2 mg/ml

11. Collagenase Type II:

Cf Rodbell, M. et al., J. Biol. Chem. 239: 375 (1964).

12. Interleukin-3 (IL-3):

Recombinant human IL-3 from *E. coli* (Yang Y. C. et al., Cell 47: 10 (1986)); contains the 133 amino acid residues including mature IL-3 and the 134 amino acid residues including the methionyl form in a ratio of approximately 1:2; calculated mol. mass approximately 17.5 kD; specific activity $1 \times 10^3$ U/µg; (R&D Catalogue No. 203-IL)

13. Macrophage-colony stimulating factor (M-CSF)

Recombinant human M-CSF from *E. coli*; contains as monomer (18.5 kD) 135 amino acid residues including the N-terminal methionine; is present as a homodimer with a molar mass of 37 kD; (SIGMA Catalogue No. M 6518)

14. Antibodies:

The antibodies used in the examples against the antigens CD14, CD31, CD90, CD117, CD123, CD135 are commercially available. They were obtained from the following sources:

CD14: DAKO, Monoclonal Mouse Anti-Human CD14, Monocyte, Clone TÜK4, Code No. M 0825, Lot 036 Edition 02.02.01;

CD31: PharMingen International, Monoclonal Mouse Anti-Rat CD31 (PECAM-1), Clone TLD-3A12, Catalogue No. 2271 ID, 0.5 mg;

CD90: Biozol Diagnostica, Serotec, Mouse Anti-Human CDw90, Clone No. F15-42-1, MCAP90, Batch No. 0699;

CD117: DAKO, Monoclonal Mouse Anti-Human CD117, c-kit, Clone No. 104D2, Code No. M 7140, Lot 016, Edition 04.05.00;

CD123: Research Diagnostics Inc., Mouse Anti-human CD123 antibodies, Clone 9F5, Catalogue No. RDI-CD123-9F5;

CD135: Serotec, Mouse Anti-Human CD135, MCA1843, Clone No. BV10A4H2.

EXAMPLE 1

Separation of Monocytes from Whole Blood

To avoid blood clotting and to feed the cells, 450 ml of whole blood in a 3-chamber bag set was mixed with 63 ml of a stabilizing solution, which contained for each liter of $H_2O$, 3.27 g citric acid, 26.3 g trisodium citrate, 25.5 g dextrose and 22.22 g sodium dihydroxyphosphate. The pH-value of the solution amounted to 5.6-5.8.

"Sharp centrifugation" of this mixture was then carried out to separate the blood components at 4000 rpm for 7 minutes at 20° C. This resulted in a 3-fold stratification of the corpuscular and non-corpuscular components. By inserting the set of bags into a pressing machine provided for this purpose, the erythrocytes were then pressed into the lower bag, the plasma was pressed into the upper bag, and the "Buffy-coat" remained in the middle bag, and it contained approximately 50 ml in volume.

The quantity of 50 ml freshly obtained "Buffy-coat" was then divided into 2 portions of 25 ml each, each of which was then coated with 25 ml Ficoll-Hypaque separation medium, which had been introduced into two 50 ml Falcon tubes beforehand.

This mixture was centrifuged without brake for 30 minutes at 2500 rpm. Thereafter, erythrocytes and dead cells still present in the "Buffy coat" lay below the Ficoll phase while the white blood cells including the monocytes are separated as a white interphase on the Ficoll.

The white interphase of the monocytes was then carefully pipetted off and was mixed with 10 ml of phosphate buffered physiological saline (PBS).

This mixture was then centrifuged with brake three times for 10 minutes at 1800 rpm; the supernatant was pipetted off after each centrifugation and fresh PBS was filled up.

The cell sediment collected on the base of the centrifugation vessel (Falcon tube) contained the mononuclear cell fraction, i.e., the monocytes.

EXAMPLE 2

Propagation and Dedifferentiation of the Monocytes

The cultivation and propagation of the monocytes on the one hand and the dedifferentiation of the cells on the other hand were carried out in one step in nutrient medium of the following composition:

| | |
|---|---|
| RPMI 1640 medium | 440 ml |
| Fetal calf serum (FCS) | 50 ml |
| Penicillin/Streptomycin solution | 5 ml |
| 2-Mercaptoethanol (Stock solution) | 5 ml |
| Total volume | 500 ml |

The nutrient medium further contained 2.5 µg/500 ml of M-CSF and 0.2 µg/500 ml interleukin-3 (IL-3).

The monocytes isolated in Example 1 were transferred into 5 chambers of a 6-chamber well plate (30 mm diameter per well) in a quantity of approximately $10^5$ cells per chamber in each case, and filled up in each case with 2 ml of the above-mentioned nutrient medium. The 6-well plate was previously filled with pure, inactivated FCS and the FCS was decanted after approximately 7 hours, in order to obtain an FCS-coated plate in this way. The cell number for the exact dose per well was determined according to a known process, cf. Hay R. J., "Cell Quantification and Characterization" in Methods of Tissue Engineering, Academic Press 2002, Chapter 4, Pages 55-84.

The 6-well plate was covered with its lid and stored for 6 days in an incubator at 37° C. The cells settled to the bottom of the chambers after 24 hours. Every second day the supernatant was pipetted off and the chambers of the 6-well plate were again each filled up with 2 ml of fresh nutrient medium.

On the 6th day 2 ml of 70% ethanol was introduced into the 6-well plate's 6th chamber which had remained free, the plate was again closed and was stored for a further 10 hours at 37° C. in the incubator.

Subsequently, 1 ml of a trypsin solution diluted 1:10 with PBS were pipetted into each of the chambers of the well plate which contained cells. The closed well plate was placed for 5 minutes at 37° C. under 5% $CO_2$ in the incubator.

The trypsin activity was subsequently blocked by the addition of 2 ml of RPMI 1640 medium to each of the wells. The total supernatant in each of the chambers (1 ml trypsin+2 ml medium) was pipetted off, pooled in a 15 ml Falcon tube and centrifuged for 10 minutes at 1800 rpm. The supernatant was then discarded and the precipitate was mixed with fresh RPMI 1640 medium (2 ml/$10^5$ cells).

This cell suspension could be directly used for differentiation into different target cells.

Alternatively, after centrifugation and discarding of the trypsin-containing supernatant the cells were mixed with DMSO/FCS as a freezing medium and deep-frozen at a concentration of $10^6$/ml.

The freezing medium contained 95% FCS and 5% DMSO. In each case approximately $10^6$ cells were taken up in 1 ml of the medium and cooled down in the following steps:

30 minutes on ice;

2 hours at −20° C. in pre-cooled Styropor boxes;

24 hours at −80° C. in Styropor;

Storage in tubes in liquid nitrogen ($N_2$) at −180° C.

For immune-histochemical phenotyping of the cell population of dedifferentiated programmable stem cells of monocytic origin, generated according to the above process, in each case $10^5$ cells were taken and fixed as a cytospin preparation on slides for further histochemical staining (Watson, P. "A slide centrifuge; an apparatus for concentrating cells in suspension on a microscope slide." J. Lab. Clin. Med., 68: 494-501 (1966)). After this the cells could be stained using the technique illustrated by Cordell, J. L., et al., (Literature, see below) with APAAP red complex. If not indicated otherwise, the added primary antibody was diluted 1:100 with PBS, and in each case 200 µl of this concentration of antibodies was used. Monoclonal antibodies were used as primary antibodies against the cell antigen epitopes listed in Table 1. FIG. 6 shows stained cytospin preparations and the corresponding proof of the stem cell markers CD90, CD117, CD123 and CD135.

Literature Relating to Staining Technique:

Cordell J. L., et al. "Immunoenzymatic labeling of monoclonal antibodies using immune complexes of alkaline phosphatase and monoclonal anti-alkaline phosphatase (APAAP complexes)." J. Histochem. Cytochem. 32: 219-229 (1984).

Literature Relating to the Markers:

CD14

Ferrero E., Goyert S. M. "Nucleotide sequence of the gene encoding the monocyte differentiation antigen, CD14", Nucleic Acids Res. 16: 4173-4173 (1988).

CD31

Newman P. J., Berndt M. C., Gorski J., White J. C. II, Lyman S., Paddock C., Muller W. A. "PECAM-1 (CD31) cloning and relation to adhesion molecules of the immunoglobulin gene superfamily", Science 247: 1219-1222 (1990).

CD90

Seki T., Spurr N., Obata F., Goyert S., Goodfellow P., Silver J. "The human thy-1 gene: structure and chromosomal location", Proc. Natl. Acad. Sci. USA 82: 6657-6661 (1985).

CD117

Yarden Y., Kuang W.-J., Yang-Feng T., Coussels L., Munemitsu S., Dull T. J., Chen E., Schlessinger J., Francke U., Ullrich A. "Human proto-oncogene c-kit: a new cell surface receptor tyrosine kinase for an unidentified ligand." EMBO J. 6: 3341-3351 (1987).

CD123

Kitamura T., Sato N., Arai K., Miyajima A. "expression cloning of the human IL-3 receptor cDNA reveals a shared beta subunit for the human IL-3 and GM-CSF receptors." Cell 66: 165-1174 (1991).

CD135

Small D., Levenstein M., Kim E., Carow C., Amn S., Rockwell P., Witte L., Burrow C., Ratajazak M. Z., Gewirtz A. M., Civin C. I., "STK-1, the human homolog of Flk-2/Flt-3, is selectively expressed in CD34+ human bone marrow cells and is involved in the proliferation of early progenitor/stem cells." Proc. Natl. Acad. Sci. USA 91: 459-463 (1994).

TABLE 1

Antigen expression of the stem cells according to the invention

| Antigen | Color reaction |
| --- | --- |
| Stem cell marker | |
| CD90 | ++ |
| CD117 | + |
| CD123 | ++ |
| CD135 | +(+) |
| Differentiation marker | |
| CD14 (monocytes) | + |

The graduation indicated corresponds to the detected antigen positivity, which becomes apparent from Day 4 to Day 9 after cultivation of the monocytes in the correspondingly specified media and was carried out via microscopic comparison of the respective cytospin colorationswith the negative control (coloration observed without primary antibodies).
+ clear color reaction of the cells with the primary antibody;
++ strong color reaction of the cells with the primary antibody.

Only cytospin preparations which had more than 70% vital cells with typical stem cell morphology (cf. FIG. 6) were evaluated. Less than 1% of these cells expressed the CD34 antigen.

EXAMPLE 3

Production of Neurons and Glia Cells From Adult Stem Cells

The production of neurons and glia cells was carried out in petri dishes with a diameter of 100 mm. To prepare the petri dishes, 5 ml of pure inactivated fetal calf serum (FCS) was introduced into each dish, so that the bottom was covered. After 7 hours, the proportion of FCS not adhering to the bottom of the petri dish was pipetted off. Approximately $10^6$ of the cells produced in accordance with Example 2 were introduced into one of the prepared petri dishes and 10 ml of nutrient medium of the following composition was added:

| | |
|---|---:|
| DMEM solution | 440 ml |
| Fetal calf serum (FCS) | 50 ml |
| l-Glutamine | 5 ml |
| Penicillin (100 U/l)/Streptomycin (100 μg/l) solution | 5 ml |
| Total volume | 500 ml |

The nutrient medium further contained retinic acid in a quantity of $1 \times 10^6$ M/500 ml.

The reprogramming/differentiation of the stem cells used into neurons and glia cells took place within 10 days, the medium being changed at intervals of approximately 3 days. After this period, the cells were mostly adhering to the bottom of the chamber and could be detached by brief trypsinization from the bottom of the plate in a manner analogous to that previously illustrated for the stem cells.

EXAMPLE 4

Evidence of Neuronal Precursor Cells, Neurons and Glia Cells

For the later immunohistochemical characterization of the target cells induced by the dedifferentiated programmable stem cells, the stem cells generated from monocytes ($10^5$ cells/glass lid) were applied to glass lids (20 mm×20 mm), which were placed on the bottom of the 6-well plates (30 mm diameter per chamber) and cultivated with the nutrient medium (2 ml) per well plate. After the respective target cells were differentiated, these were fixed as follows: After removal of the nutrient medium (supernatant) the cultivated target cells were fixed by the addition of 2 ml Methanol, which took effect over 10 minutes. Subsequently the ethanol was pipetted off, and the well plates were washed twice with PBS (2 ml in each case). After this, the cells could be stained with APAAP red complex using the technique illustrated by Cordell, J. L., et al., "Immunoenzymatic labeling monoclonal antibodies using immune complexes of alkaline phosphatase and monoclonal anti-alkaline phosphatase (APAAP complexes)." J. Histochem. Cytochem. 32: 219-229 (1994). Unless otherwise specified, the added primary antibody was diluted 1:100 with PBS, in each case 200 μl of this concentration of antibodies were pipetted into each of the 6 wells.

Neuronal precursor cells were detected by staining the cells with the antibody against the S100-antigen, cf. middle picture of FIG. 1 (x200).

Neurons were detected by specific expression of synaptophysin MAP2 (microtubular associated protein 2) or neurofilament 68 with the corresponding specific antibodies (primary antibody diluted 1:300 with PBS), right-hand picture of FIG. 1, x200.

Glia cells, such as for example astrocytes, were identified by detection of GFAP (glial fibrillary associated protein) (primary antibody diluted 1:200 with PBS), left-hand picture of FIG. 1, x200.

The separation of neurons and glia cells was carried out using antibodies specific against MAP2 (neurons) or GFAP (glia cells), by means of MACS (Magnetic Activated Cell Sorting) according to the process as illustrated for example in Carmiol S., "Cell Isolation and Selection" Methods of Tissue Engineering, Academic Press 2002, Chapter 2, Pages 19-35. The cell types made visible by staining are shown in FIG. 1.

EXAMPLE 5

Production of Endothelial Cells From Dedifferentiated Programmable Adult Stem Cells of Monocytic Origin For the cultivation of endothelial cells, Matrigel® (Beckton and Dickinson, Heidelberg, Del.) was used as matrix. This matrix consists of fibronectin, laminin and collagens I and IV.

The frozen matrix was slowly thawed at 4° C. in a refrigerator over a period of 12 hours. During this period its state changed, i.e., the originally solid matrix became spongy/liquid. In this state it was introduced into a 48-well plate (10 mm diameter per well) in such a manner, that the bottom of each of the wells was covered.

After application, the plate was kept for 30 minutes at room temperature, until the gel had solidified at the bottom as an adherent layer.

Subsequently approximately $1 \times 10^2$ cells per well were incubated on Matrigel® with addition of the nutrient medium (as illustrated in Example 2).

After 4-5 days the first tubular cell strands appeared, which developed after 6-8 days into three-dimensional cell networks. On the cells, the endothelial markers CD31 and factor VII could be identified with the respective specific primary antibodies (200 μl, in each case diluted to 1:100 with PBS).

In an alternative process the liquefied matrix was applied to a vessel-prosthesis, which was then coated with the dedifferentiated programmable adult stem cells according to Example 2. After approximately 6 days a lawn of endothelial cells could be identified, which coated the prosthesis in a circular manner.

The endothelial cells made visible by staining with corresponding endothelium-specific antibodies (see above) are shown in FIG. 2. In the middle picture, the cells are shown after 5-days incubation on Matrigel®. First tubular strands combine individual cell aggregates. The dark-brown marked cells express CD31 antigen (x200 with yellow filter). After 8 days there is an increasing formation of three-dimensional network structures takes place (anti-CD31 antigen staining, x200 with yellow filter). After 12 days the newly differentiated CD31$^+$ cells, which had been cultivated on Matrigel®, form a vessel-like three-dimensional tube with multi-layer wall structures, which is already morphologically reminiscent of a vessel. It is recognized, that now almost all the cells express the CD31 antigen (CD31 coloration, x 200, blue filter, left-hand picture).

EXAMPLE 6

Production of Fat Cells (Adipocytes)

A: For the programming/differentiation of the adult stem cells according to Example 2 into fat cells, a conditioned medium was first generated. For this purpose 20 g of an autologous fat tissue, i.e., fat tissue from the same human donor, from the blood of whom the monocytes also originated, was processed as follows:

At first, the fat tissue was crushed in a petri dish and the crushed tissue pieces were passed through a sieve (diameter of holes 100 μm).

The suspension thus obtained was then transferred into a petri dish with a diameter of 100 mm and 10 ml DMEM-medium with a content of 30 mg collagenase type II were added. The mixture was left for approximately 60 minutes at room temperature (22° C.±2° C.) to allow the collagenase to take effect on the fat cells.

Subsequently the mixture was transferred to 50-ml Falcon tubes, and the tubes were centrifuged for 10 minutes at 1800 rpm.

After centrifugation the supernatant was discarded and the cell pellet consisting of adipocytes and precursor cells was taken up in 8 ml of a medium of the following composition and incubated in petri dishes (diameter 100 mm) for 10 days at 37° C. in an incubator:

| | |
|---|---|
| DMEM solution | 444.5 ml |
| Fetal calf serum (FCS) | 50 ml |
| Insulin solution | 0.5 ml |
| Penicillin (100 U/l)/Streptomycin (100 µg/l) solution | 5 ml |
| Total volume | 500 ml |

The insulin solution contained 18 mg insulin (Sigma 1-0259) dissolved in 2 ml of acetic water (consisting of 40 ml of $H_2O$ and 0.4 ml of glacial acetic acid). The solution is diluted 1:10 with acetic water.

During the incubation over 10 days, the fat-cell-conditioned medium (FCCM) formed a supernatant. The supernatant was replaced with fresh nutrient medium after 2 to 4 days in each case. The FCCM obtained during each change of medium was subjected to sterile filtration and stored at −20° C. Subsequently 10 ml of the FCCM illustrated above were introduced into a petri dish (diameter 100 mm) together with approximately $10^6$ stem cells according to Example 2. The first precursor cells containing fat vacuoles became visible after 4 days (FIG. 3A). After 6 days, single adipocytes appeared, which could be stained with Sudan red (FIGS. 3B and C). After 10 days there was typical aggregation and cluster formation of these cells, which at this step could already be observed macroscopically as fat tissue (FIG. 3D).

The fat cells made visible by staining in FIGS. 3A-3D thus differ quite considerably from the controls 3E and 3F: FIG. 3E shows the cells of monocytic origin, which were cultivated in the nutrient medium (as indicated in Example 2) for 6 days, but without the addition of IL-3 and 2-mercaptoethanol to the nutrient medium. This was followed by the addition of the FCCM. These cells were not capable of differentiating into fat cells. Figure F shows cells, which were cultivated for 6 days with complete medium (according to Example 2), and which were then treated for a further 6 days with nutrient medium instead of with FCCM (according to Example 2). The FCCM thus contains components which are required to provide the signal for differentiation into fat cells.

The staining of the cells with Sudan red in FIGS. 3A, B, C and D took place according to the method illustrated by Patrick Jr., C. W., et al. "Epithelial Cell Culture: Breast", in Methods of Tissue Engineering, Academic Press 2002, Chapter 4, Pages 141-149.

B: In addition to the phenotyping of the fat cells by staining with Sudan red, molecular-biological characterization of the fat cells was carried out at the mRNA level, in order to check whether the genetic program of the fat cells, after corresponding programming with the fat-cell-conditioning medium used, undergoes a corresponding alteration, and typical messenger-ribonucleic acid (mRNA) transcripts, illustrated for fat cells can be identified in the fat cells programmed from programmable monocytes. Two mRNA sequences typical of fat cell metabolism were amplified by means of polymerase chain reaction (PCR) from isolated RNA samples from dedifferentiated programmable stem cells of monocytic origin and, in a parallel test mixture, amplified from the programmed fat cells, namely "peroxisome proliferative activated receptor gamma" (PPARG)-mRNA, (Tontonoz, P., et al. "Stimulation of adipogenesis in fibroblasts by PPAR gamma 2, a lipid-activated transcription factor." Cell 79: 1147-1156 (1994), gene bank access code number; NM_005037) and "leptin (obesity homolog, mouse)"-mRNA, (Zhang Y., et al. "Positional cloning of the mouse obese gene and its human homologue." Nature 372: 425-432 (1994), gene bank, access code number: NM_000320).

The RNA-isolation needed for this purpose, the reverse transcription method and the conditions of the PCR amplification of the desired mRNA sequences were carried out as illustrated in detail in the state of the art, see Ungefroren H., et al., "Human pancreatic adenocarcinomas express Fas and Fas ligand yet are resistant to Fas-mediated apoptosis", Cancer Res. 58: 1741-1749 (1998).

For this purpose the respective primers produced for the PCR amplification were selected so that the forward- and reverse primers bind to mRNA sequences, whose homologous regions in the chromosomal gene lie in two different exons and are separated from one another by a large intron. It could thereby be ensured that the amplification fragment obtained originates from the mRNA contained in the cell and not from the sequence present in the chromosomal DNA. In particular the following primer sequences were selected for PPAR-γ and for leptin:

PPAR-γ: forward-primer; 265-288 (corresponding gene sequence in exon 1), reverse-primer: 487-465 (corresponding gene sequence in exon 2), this results in an amplification fragment of 487-265 bp=223 bp, see FIG. 3G. As further shown by FIG. 3G traces of transcribed PPAR-γ-specific mRNA can already be identified in the programmable stem cell and in the tumor cell line HL-60 (of a human promyeloic leukemia cell line), although with significantly narrower signal bands than in the fat cell itself. In contrast, the fat-cell-specific protein leptin can only be detected in the fat cells derived from the programmable stem cells at mRNA level by reverse-transcriptase PCR.

The programmable stem cells (progr. stem cell) used as a control and the human tumor cell lines HL-60, Panc-1 and WI-38 transcribe no leptin. As negative controls all the samples without the addition of the reverse transcriptase (fat cell/-RT) and $H_2O$-samples were simultaneously co-determined. By identification of the GAPDH "house-keeping" gene in the positive controls, it is ensured that the respective PCR amplification steps were properly carried out in the individual mixtures.

EXAMPLE 7

Production of Liver Cells (Hepatocytes)

A: For the programming of the dedifferentiated programmable stem cells of monocytic origin according to Example 2 into liver cells, a conditioned medium was first generated. For this purpose 40 g of human liver tissue was processed as follows.

First the liver tissue was rinsed several times in PBS, to essentially remove erythrocytes. The tissue was then crushed in a petri dish and incubated with a dissociation solution for approximately 45 minutes at room temperature. The dissociation solution consisted of 40 ml PBS (phosphate buffered saline), 10 ml of a trypsin solution diluted 1:10 with PBS and 30 mg collagenase type II (Rodbel M., et al. J. Biol. Chem. 239: 375 (1964)). After a 45-minute incubation, the tissue pieces were passed through a sieve (see Example 6).

The mixture was then transferred into 50-ml Falcon tubes, filled up to 50 ml with PBS and centrifuged for 10 minutes at 1800 rpm.

After centrifugation the supernatant was discarded and the cell pellet containing the liver cells was again washed with 50 ml PBS and centrifuged. The supernatant thus produced was again discarded and the cell pellet taken up in 25 ml of a medium of the following composition and incubated in cell culture flasks (250 ml volume) for 10 days at 37° C. in an incubator:

Liver cell growth medium

| Liver cell growth medium, LCGM | |
| --- | --- |
| RPMI 1640 medium | 445 ml |
| Fetal calf serum (FCS) | 50 ml |
| Insulin solution | 0.5 ml |
| Penicillin (100 U/l)/Streptomycin (100 µg/l) solution | 5 ml |
| Total volume | 500 ml |

The nutrient medium contained in addition 5 µg (10 ng/ml) of epidermal growth factor (Pascall, I. C. et al., J. Mol. Endocrinol. 12: 313 (1994)). The composition of the Insulin solution was as illustrated in Example 6.

During the incubation lasting 10 days the liver cell conditioned medium (LCCM) formed as a supernatant. The supernatant was replaced by fresh nutrient medium after 2 to 4 days respectively. The respective LCCM obtained during the change of medium in each case was subjected to sterile filtration (filter with 0.2 µm pore size) and stored at −20° C.

$1 \times 10^6$ dedifferentiated stem cells were then cultivated with 10 ml of a medium of the following composition in a petri dish (Ø100 mm) or a culture flask.

Liver cell differentiation medium

| (Liver cell differentiation medium, LCDM): | |
| --- | --- |
| LCCM | 100 ml |
| Insulin solution (cf. Example 6) | 0.1 ml |
| epidermal growth factor | 1 µg |
| hepatocyte growth factor | 2 µg |

Hepatocyte growth factor (Kobayashi, Y. et al., Biochem. Biophys. Res. Commun. 220: 7 (1996)) was used in the concentration of 40 ng/ml. After a few days morphological changes towards flat, polygonal mono- or diploid cells could be observed (FIG. 4A). After 10-12 days hepatocytes arising from dedifferentiated stem cells could be identified by immune-histochemical detection of the liver-specific antigen alpha-fetoprotein (Jacobsen, G. K. et al., Am. J. Surg. Pathol. 5: 257-66 (1981)), as shown in FIGS. 4B and 4C.

B: In addition to the phenotyping of the hepatocytes by immune-histochemical identification of the alpha-fetoprotein, a molecular-biological characterization of the hepatocytes at mRNA level was carried out, in order to check whether the genetic program of the stem cells, after corresponding programming with the liver-cell-conditioning medium used undergoes a corresponding alteration, and whether messenger-ribonucleic acid (mRNA) transcripts, illustrated as typical of liver cells in the hepatocytes arising from the stem cells according to the invention can be identified. For this purpose, the presence of five different mRNA sequences typical of hepatocytes was examined by means of polymerase chain reaction (PCR) in isolated RNA samples from dedifferentiated programmable stem cells of monocytic origin and, in a parallel test sample, from the liver cells obtained by programming of the stem cells. In particular, this is the *Homo sapiens* albumin-mRNA (Lawn, R. M., et al. "The sequence of human serum albumin cDNA and its expression in *E. coli*." Nucleic Acids Res. 9: 6103-6114, (1981), gene bank access code number: NM-000477), alpha-fetoprotein-mRNA (Morinaga T., et al. "Primary structures of human alpha-fetoprotein and its mRNA." Proc. Natl. Acad. Sci. USA 80: 4604-4608 (1983), gene bank access code number: V01514), Human carbamyl phosphate synthetase I mRNA (Haraguchi, Y., et al. "Cloning and sequence of a cDNA encoding human carbamyl phosphate synthetase I: molecular analysis of hyperammonemia" Gene 107: 335-340 (1991), gene bank access code number D90282), *Homo sapiens* coagulation factor II (Thrombin, F2) mRNA (Degen, S. J. et al. "Characterization of the complementary deoxyribonucleic acid and gene coding for human prothrombin" Biochemistry 22: 2087-2097 (1983), gene bank access code number NM-000506), *Homo sapiens* coagulation factor VII (serum prothrombin conversion accelerator, F7) mRNA (NCBI Annotation Project. Direct Submission, 06 Feb. 2002, National Center for Biotechnology Information, NIH, Bethesda, Md. 20894, USA, gene bank access code number XM-027508).

The RNA-isolation necessary for this reverse transcriptase method and the conditions of the PCR amplification of the desired mRNA sequences was carried out as illustrated in detail in the state of the art, see Ungefroren H., et al., "Human pancreatic adenocarcinomas express Fas and Fas ligand yet are resistant to Fas-mediated apoptosis" Cancer Res. 58: 1741-1749 (1998).

The respective primers for the PCR amplification were selected so that the forward- and reverse primers bind to mRNA sequences whose homologous regions in the chromosomal gene lie in two different exons and are separated from one another by a large intron. In this way it could be ensured that the amplification fragment obtained originates from the mRNA contained in the cell and not from the sequence present in the chromosomal DNA.

The primer sequences indicated below were selected; the results of the respective PCR analyses are reproduced in FIG. 4D. The dedifferentiated programmable stem cells according to the invention, are designated there as "progr. stem cell" and the hepatocytes derived by programming of these as "progr. hepatocyte".

Alpha-fetoprotein: forward primer: 1458-1478 (corresponding gene sequence in Exon 1), reverse primer: 1758-1735 (corresponding gene sequence in Exon 2), this results in an amplification fragment of 1758-1458 bp=391 bp, see FIG. 4D.

As shown in FIG. 4, the programmable stem cell (progr. stem cell), which itself contains no identifiable specific mRNA transcripts for alpha-fetoprotein, can be programmed into a hepatocyte (progr. hepatocyte), which contains this mRNA transcript (positive band with a molecular weight of 301 bp). This also explains the immune-histochemical detectability of the alpha-fetoprotein, as shown in FIGS. 4B and 4C.

The positive controls, namely human liver tissue and the liver tumor cell line HepG2 also transcribe alpha-fetoprotein-specific mRNA, as the 301 bp bands confirm.

Albumin: forward primer: 1450-1473 (corresponding gene sequence in exon 1), reverse primer: 1868-1844 (corresponding gene sequence in Exon 2), this resulted in an amplification fragment of 1868-1450 bp=419 bp, see FIG. 4D.

FIG. 4D shows traces of transcribed albumin-specific mRNA already in the programmable stem cell, while the hepatocytes obtained by programming of the stem cells and normal liver tissue as well as the tumor cell line HepG2, which were both used as positive controls, strongly express the mRNA, as can be recognized by clear bands.

The carbamyl phosphatase synthetase I: forward primer: 3135-3157 (corresponding gene sequence in exon 1), reverse primer: 4635-4613 (corresponding gene sequence in exon 2), this results in an amplification fragment of 4635-3135=1500 bp, see FIG. 4D.

The carbamyl phosphate synthetase I represents an enzyme specific to the hepatocytes, which plays an important role in the metabolization of urea in the "urea cycle". This detoxification function is guaranteed by functioning hepatocytes. As FIG. 4D shows, both in the hepatocytes generated from programmable stem cells and also in the positive controls (human liver tissue and the HepG2-tumor cell line), the mRNA bands (1500 bp) specific to carbamyl phosphate synthetase I can be identified. The somewhat weaker expression of the mRNA bands for the programmed hepatocytes (progr. hepatocyte) is due to the lack of substrate available in the culture dish.

Clotting factor II: forward primer: 1458-1481 (corresponding gene sequence in exon 1), reverse primer: 1901-1877 (corresponding gene sequence in exon 2), this results in an amplification fragment of 1901-1458=444 bp, see FIG. 4D.

This likewise hepatocyte-specific protein can only be detected in the programmed hepatocyte (progr. hepatocyte) and in the positive control from human liver tissue at mRNA level by 444 bp band expression, whereas the programmable stem cell (progr. stem cell) does not show this band, i.e., the gene is not transcribed there, as can be seen in FIG. 4D.

Clotting factor VII: forward primer: 725-747 (corresponding gene sequence in exon 1), reverse primer: 1289-1268 (corresponding gene sequence in exon 2), this results in an amplification fragment of 1289-725=565 bp, see FIG. 4D.

As in the case of clotting factor II, also this protein is only transcribed in programmed hepatocytes (progr. hepatocyte) and in the positive control (human liver tissue) (see bands at 656 bp), although weaker than clotting factor II. Neither the programmable stem cell nor the negative control ($H_2O$) show this specific mRNA band.

Glycerine aldehyde dehydrogenase: This gene, also referred to as a "house-keeping gene" can be detected in every eukaryotic cell and serves as a control whether PCR amplification was properly carried out in all samples; it is co-determined in parallel and results from the addition of a definite quantity of RNA from the respective cell samples.

As negative control $H_2O$ samples were simultaneously co-determined in all tests. If the $H_2O$ is not contaminated with RNA, no amplificate is produced during the PCR and no band is detectable (thus serves as counter-control).

EXAMPLE 8

Production of Skin Cells (Keratinocytes)

For the programming of dedifferentiated programmable stem cells of monocytic origin according to Example 2 in skin cells a conditioned medium was first generated. For this purpose, 1-2 $cm^2$ of complete human skin was processed as follows.

The skin material was first freed from the subcutis under sterile conditions. The tissue was then washed a total of ten times with PBS in a sterile container by vigorous shaking. After the second washing, the tissue was again freed from demarked connective tissue residues.

The skin material was then placed in a petri dish with a diameter of 60 mm, mixed with 3 ml of a trypsin solution diluted 1:10 with PBS and cut into small pieces (approximately 0.5 to 1 $mm^3$). After this, 3 ml of the trypsin solution diluted 1:100 with PBS was again added to the mixture and the mixture was incubated at 37° C. for 60 minutes with intermittent shaking.

The larger particles were then allowed to settle and the supernatant containing the keratinocytes was poured off and centrifuged at 800 rpm for 5 minutes. The supernatant now produced was pipetted off and the cell pellet was taken up in 3 ml of a medium of the following composition and incubated in petri dishes (Ø100 mm) for 15 days in an incubator at 37° C.

| Keratinocyte growth medium | |
|---|---|
| (Keratinocyte growth medium, KGM): | |
| DMEM | 333.5 ml |
| Fetal Calf serum (FCS) | 50 ml |
| Ham's F12 medium | 111 ml |
| Penicillin (100 U/l)/Streptomycin (100 µg/l) solution | 5 ml |
| Insulin solution (cf. Example 6) | 0.5 ml |
| Total volume | 500 ml |

The nutrient medium contained 5 µg of epidermal growth factor (for exact specification see Example 7) and 5 mg of hydrocortisone (Ref. Merck Index: 12, 4828).

During the 15 days' incubation period, the keratinocyte-cell-conditioned medium KCCM formed as supernatant. The supernatant was replaced with fresh nutrient medium after 2-4 days in each case. The KCCM obtained during each change of medium was subjected to sterile filtration and stored at −20° C.

$1 \times 10^6$ dedifferentiated stem cells were then cultivated with 10 ml of a mediums of the following composition in a petri dish (Ø 100 mm) or a culture flask.

| Keratinocyte differentiation medium | |
|---|---|
| (Keratinocyte differentiation medium, KDM) | |
| KCCM | 100 ml |
| Insulin solution (cf. Example 6) | 0.5 ml |
| epidermal growth factor (EGF) | 1 µg |
| Hydrocortisone | 1 mg |
| keratinocyte growth factor (KGF) | 2.5 µg |

Keratinocyte growth factor was used in a concentration of 25 ng/ml, as illustrated by Finch et al., Gastroenterology 110: 441 (1996).

After a few days a morphological change in the cells could be observed. After 6 days the keratinocyte-specific antigens, cytokeratin 5 and 6, which are both bound by the primary antibody used, (Exp. Cell. Res. 162: 114 (1986)) could be detected (FIG. 5A). After 10 days a cell adherence of the clearly larger individual cells already took place in culture, which made it possible to identify a visible cell tissue combination of confluent cells (FIG. 5B).

EXAMPLE 9

Production of Insulin-producing Cells from Differentiated Programmed Stem Cells

The production of insulin-producing cells was conducted in culture flasks with a volume of approximately 250 ml and flat walls (T75 cell culture flasks). Approximately $5 \times 10^6$ of the cells produced according to Example 13 were suspended in approximately 5 ml of the culture medium indicated below (differentiation medium for insulin producing cells) and after being introduced into the flasks, mixed with a further 15 ml of culture medium. For the differentiation of the cells, the flasks were incubated in a horizontal position in an incubator at 37° C. and 5% $CO_2$.

Culture medium (modified according to Rameya V. K. et al., Nature Medicine, 6 (3), 278-282 (2000)):

| | |
|---|---|
| RPMI 1640 | 445 ml |
| Fetal calf serum (FCS) | 50 ml |
| Penicillin (100 U/l)/Streptomycin (100 µg/l) solution | 5 ml |
| Nicotinamide | 620 mg |
| Glucose | 360 mg |
| Total volume | 500 ml |

The nutrient medium further contained the epidermal growth factor in a quantity of 10 ng/ml and the hepatocyte growth factor in a quantity of 20 ng/ml.

Within the first hour the cells adhere to the bottom of the culture vessel. The differentiation of the stem cells was monitored by reference to insulin production. For this purpose the culture medium was changed at intervals of approximately 2 to 3 days, the cell supernatant was collected each time, and frozen at −20° C. The cells adhering to the bottom of the culture flask could be detached by tryptinization as illustrated in Example 2.

The insulin content of the supernatant collected at the different times was measured by means of ELISA (Enzyme-linked-immunosorbent-assay) against human insulin (Bruhn H. D., Folsch U. R. (Eds.), Lehrbuch der Labormedizin: Grundlagen, Diagnostik, Klinik Pathobiochemie [*Textbook of Laboratory Medicine, Principles, Diagnosis, Clinical Pathobiochemistry*] (1999), Page 189) and compared with the blank reading of the medium. The results reproduced in FIG. 8 show that the cells have reached the maximum level of insulin production after 14 days in culture. The insulin quantities produced by the cells treated in the course of the differentiation increased after 14 days to 3 µU/ml, while no human insulin was detectable in the control medium. The bars in FIG. 8 each represent three separate values each determined from three independent individual experiments.

Next to the determination of the insulin production in the deprogrammed stem cells, which were differentiated into insulin producing cells according to the invention, the portion of insulin-producing cells were determined which still expressed the monocyte-specific surface antigen CD14 also 3 weeks after conducting the dedifferentiation. It was found that on a great portion of these cells (about 30 to 40%) the monocyte-specific antigen CD14 was detectable also after 3 weeks.

EXAMPLE 10

Alternative Method for the Production of Hepatocytes from Dedifferentiated Programmable Stem Cells As an alternative to the use of hepatocyte-conditioned medium (LCCM), as illustrated in Example 7, the differentiation of the stem cells into hepatocytes was induced by the nutrient medium (Ha) indicated below. The production of hepatocytes from stem cells in turn took place in culture flasks with a volume of approximately 250 ml and flat walls (T75-cell culture flasks). Approximately $5 \times 10^6$ of the cells produced according to Example 13 were introduced into approximately 5 ml of the improved culture medium indicated below (Ha, differentiation medium for hepatocytes) and after being introduced into the flasks, mixed with a further 15 ml of culture medium. For the differentiation of the cells, the flasks were incubated in a horizontal position in an incubator at 37° C. and 5% $CO_2$.

Differentiation medium for hepatocytes (Ha) (modified according to Schwarz et al., "Multipotent adult progenitor cells from bone marrow differentiate into functional hepatocyte-like cells", J. Clin. Invest. 10 (109), 1291-1302 (2002)):

| | |
|---|---|
| RPMI 1640 | 445 ml |
| Fetal calf serum (FCS) | 50 ml |
| Penicillin (100 U/l)/Streptomycin (100 µg/l) solution | 5 ml |
| Total volume | 500 ml |

The nutrient medium also contained fibroblast growth factor-4 (FGF-4) in a quantity of 3 ng/ml.

Within the first hour the cells adhere to the bottom of the culture vessel. The differentiation of the stem cells was monitored with regard to albumin production. For this purpose the culture medium was changed at intervals of approximately 2 to 3 days, the cell supernatant collected each time, and frozen at −20° C. The cells adhering to the base of the culture flask could be detached by tryptinization as illustrated in Example 2.

The albumin content of the supernatant collected at the different times was measured by means of ELISA (Enzyme-linked-immunosorbent-assay) for human albumin (according to the protocol of Bethyl Laboratories Inc. and according to Schwarz et al., loc. cit.) and compared with the blank reading of the medium. The results presented in FIG. 9 show that the albumin production of the cells during the period of 14 to 28 days in culture remained approximately constant. The measurements were carried out on days 0 (blank reading of the medium), 14, 21, 28 and 30 relative to the time of addition of the Ha medium. The values determined in each case amounted to ca. 5 ng/ml, 450 ng/ml, 425 ng/ml, 440 ng/ml and 165 ng/ml. The bars in FIG. 9 each represent three separate values each determined from three independent individual experiments.

EXAMPLE 11

Determination of the Co-expression of Albumin and of the Monocyte-specific Antigen CD14 in Hepatocytes Derived from Dedifferentiated Stem Cells The determination of the co-expression of albumin and of the monocyte-specific antigen CD14 in hepatocytes derived from dedifferentiated stem cells was carried out on the one hand by double-staining (A) and on the other hand by FACS analysis (B).
A) Stem cells according to the invention differentiated into hepatocytes according to Example 10 were cultivated on cover glasses in a 6-well plate and fixed with methanol as illustrated in Example 4. A double-staining was then carried out, in order to detect the simultaneous expression of the antigen CD14 (phenotype marker of monocytes) on the one hand and of albumin (liver-specific marker) on the other hand.
  For this purpose the cells were first incubated as illustrated in Example 4 with a primary antibody against human albumin (guinea pig vs. human albumin) in a 1:50 dilution in PBS. Following a washing step, the cells were then incubated for 45 minutes with a secondary antibody mouse anti-rat, which binds the guinea pig antibodies, also in a 1:50 dilution in PBS. The staining process was then carried out according to Example 4 using the method of Cordell J. L., et al. (loc. cit.) with APAAP red complex.
  For the second staining step, the cells were then incubated with the primary anti-body, mouse anti-human-CD14, and following a washing step according to Example 4 stained with the ABC Streptavidin KIT of Vectastain (Vector) using the method of Hsu, S. M., et al. "The use of antiavidin antibody and avidin-biotin-peroxidase complex in immunoperoxidase technics" Am. J. Clin. Pathol. 75 (6): 816-821 (1981) with dem DAB-Complex (brown) (Vector Laboratories).
  Nucleus counter-staining with haemalaun was then carried out as illustrated in Example 4, followed by embedding in Kaiser's glycerol gelatin.
  The results are shown in FIG. 10. The figure shows the expression of the antigen CD14 as brown color, which slowly decreases parallel to the morphological transformation of the cells into hepatocytes, while the albumin expression as red color increases with the increasing maturation of the hepatocytes. Picture No. 4 in FIG. 10 shows the cells after three weeks stimulation with the hepatocyte-conditioned medium.
B) Parallel with the double marking, the stem cells differentiated into hepatocytes according to the invention were subjected to FACS (fluorescence-activated cell sorting) analysis.
  The stem cells differentiated into hepatocytes according to the invention according to Example 10 were first harvested by mechanical detachment of the cells from the culture flask using a cell scraper. The cells were carefully rinsed from the flask with PBS and washed twice, each time in 10 ml of PBS-solution. For this purpose the cell suspensions in the PBS solution were introduced into a 15-ml centrifuge tube and precipitated at 1600 rpm. The resultant cell sediment was diluted with PBS, such that exactly $1 \times 10^5$ cells were present in 100 µl PBS.
  10 µl of each of FITC-marked anti-CD14 antibodies (BD Pharmingen) or FITC-marked anti-albumin antibodies (Beckmann) and FITC-marked non-specific IgG1 mouse anti-human antibodies were then added to this cell suspension. After an incubation period of 20 minutes the cells were resuspended twice in 500 µl PBS and each precipitated for 5 minutes at 1600 rpm and then finally taken up in 200 µl PBS. After resuspension of the cells, fluorescence was measured with a BD FACScalibur flow cytometer from the company BD Biosciences (Franklin Lakes, N.J.) (cf. Bruhn H. D., Fölsch U. R. (Eds.), Lehrbuch der Labormedizin: Grundlagen, Diagnostik, Klinik Pathobiochemie [Textbook of Laboratory Medicine, Principles, Diagnosis, Clinical Pathobiochemistry], 395-403 (1999); and Holzer U. et al., "Differential antigen sensitivity and costimulatory requirements in human Th1 and Th2 antigen-specific CD4(+) cells with similar TCR avidity" J. Immunol. 170 (3): 1218-1223 (2003)). The evaluation of the results was carried out using the Microsoft WinMDI program with reference to Marquez M. G., et al. "Flow cytometric analysis of intestinal intraepithelial lymphocytes in a model of immunodeficiency in Wistar rats." Cytometry 41 (2): 1.15-122 (2000).
  The results of the FACS-Analysis are reproduced in FIG. 11. The figure shows the expression of the CD14 (top row) and of the albumin antigen (bottom row), which was measured in dedifferentiated monocytes (left-hand column) and in the stem cells differentiated into hepatocytes according to the invention (right-hand column). In dedifferentiated monocytes a strong expression of CD14, but no expression of albumin could be detected, while in the hepatocytes developed from dedifferentiated monocytes a weaker expression of the CD14 and a very strong expression of the albumin was detectable.

EXAMPLE 12

In Vivo Use of Dedifferentiated Programmed Stem Cells of Monocytic Origin

In order to clarify, to what extent the programmable stem cells in vivo after injection via the portal vein into the liver of a genetically identical recipient animal undergo a specific differentiation via the signal-providers present in the liver, livers of female LEW rats were first treated with retrorsine, in order to inhibit the hepatocytes present in the liver (liver parenchyma cells) regarding their proliferation activity (Ref. Lacone, E., et al. "Long-term, near-total liver replacement by transplantation of isolated hepatocytes in rats treated with retrorsine" Am. J. Path. 153: 319-329 (1998)).
  For this purpose the LEW rats received 30 mg of the pyrrolizidine alkaloid retrorsine, injected intraperitoneally twice within 14 days. Subsequently an 80% resection of the livers treated in this way was carried out, followed by the administration of $5 \times 10^5$ of the programmable stem cells in 1 ml PBS into the portal vein of the remaining residual liver. The stem cells had been obtained, as illustrated in Example 2, from monocytes of male LEW rats. Five days after administration of the stem cells a punch biopsy of the liver was carried out for histological assessment of the liver and to detect the cell types differentiated from the stem cells by means of fluorescence-in-situ-hybridization (FISH) with Y-chromosome-specific probes, as illustrated in detail in Hoebee, B. et al. "Isolation of rat chromosome-specific paint probes by bivariate flow sorting followed by degenerate oligonucleotide primed-PCR." Cytogenet. Cell Genet. 66: 277-282 (1994).
  FIG. 7A shows the Y-chromosome-positive (red points in the cell nucleus) hepatocytes derived from the male LEW stem cells on the 5th day after intraportal injection into retrorsine-pretreated 80%-resectioned livers of female recipient animals. The selective removal of the same liver on day 25 after stem cell injection shows the differentiation of the stem cells into hepatocytes, endothelial cells and bile duct epithelia (FIG. 7B). At this point in time, the liver has already reached its normal size, and >90% of the cells have a Y-chromosome. From this, it can be concluded, that the injected syngenic programmable stem cells of monocytic origin in are capable in vivo, of effecting a complete restoration of the liver with normal metabolic function. FIG. 7C shows in this connection the Kaplan-Meier survival curves (n=4 per group) of stem-cell-treated versus untreated recipient rats following administration of retrorsine and 80% liver resection.

Figure 7D:
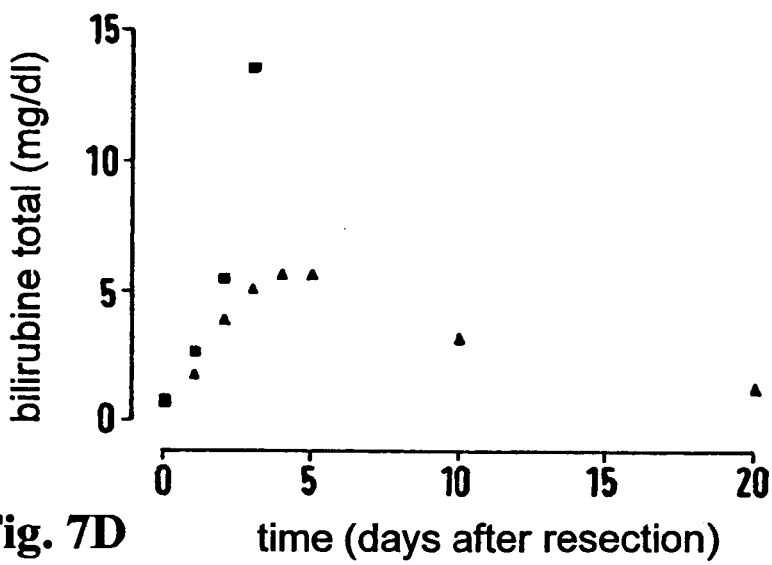
FIGS. 7D and 7E show bilirubin and ammonia as function parameters for the complete metabolic functionality of long-term surviving stem-cell-treated animals.
Figure 7E:
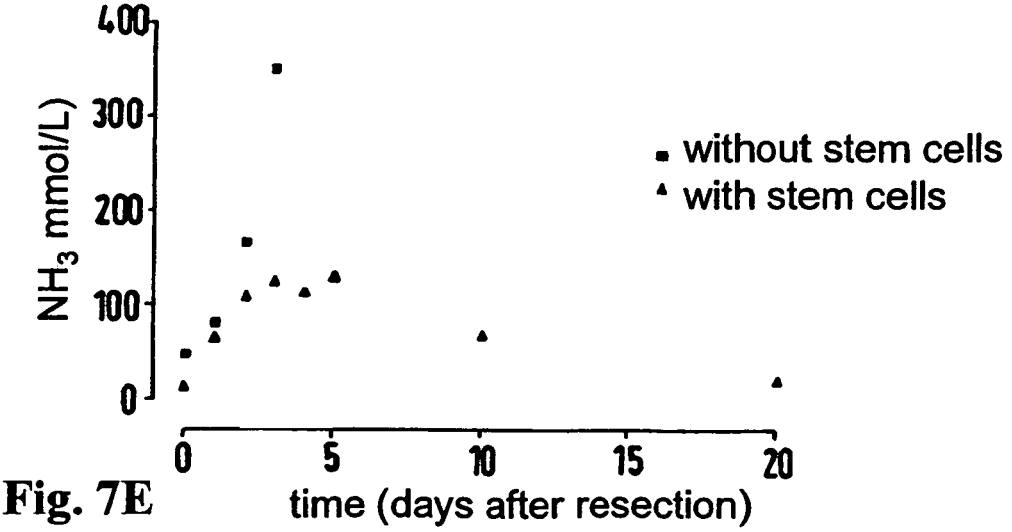

The function parameters bilirubin and ammonia ($NH_3$) prove the complete metabolic functionality of the long-term surviving stem-cell-treated animals (FIGS. 7D and 7E).

EXAMPLE 13

Propagation and Dedifferentiation of Monocytes in Cell Culture Flasks

Cultivation and propagation of the monocytes on the one hand and the dedifferentiation of the cells of the other side on a larger scale were conducted in culture flasks in the same nutrient medium, which was also used for the cultivation in well-plates (cf. Example 2). The nutrient medium contains 2.5 µg/500 ml M-CSF and 0.2 µg/500 ml interleukine 3 (IL-3).

The monocytes isolated in Example 1 were transferred to the bottom of culture flasks having a volume of 250 ml and flat walls (T75-cell culture flasks). About 10 times×$10^6$ cells were transferred into each flasks and were each filled up with 20 ml of the above indicated nutrient medium. The determination of this cell number for the exact dosing per flask was carried out according to known procedures, cf. Hay R. J., "Cell Quantification and Characterization" in Methods of Tissue Engineering, Academic Press (2002), Chapter 4, pages 55-84.

The cell culture flasks were incubated in an incubator at 37° C. for 6 days. After 24 hours, the cells settled at the bottom of the flasks. The supernatant was removed every second day and the flasks were each filled with 20 ml fresh nutrient medium.

On day 6, the flasks were rinsed twice with 10 ml PBS each, after the nutrient medium had previously been pipetted off from the flasks. Hereby, all cells were removed, which did not adhere to the bottom of the flasks. The cells growing adhere to the bottom of the flasks were subsequently removed from the bottom of the flasks with a sterile cell scraper. The separated cells were now removed from the flasks by rinsing with PBS and were pooled in a 50 ml Falcon tube and were centrifuged at 1800 rpm for 10 minutes. Thereafter, the supernatant was discarded and the sediment was resuspended in fresh RPMI 1640 medium (2 ml/$10^5$ cells).

This cell suspension could be used directly for differentiating into various target cells.

Alternatively, the cells were mixed with DMSO/FCS as freezing medium after centrifugation and were deep-frozen at a concentration of $10^6$/ml.

The freezing medium contained 95% FCS and 5% DMSO. About $10^6$ cells were taken up in 1 ml of the medium and were cooled following the subsequent steps:

30 minutes on ice;

2 hours at −20° C. in precooled styropor box;

24 hours at −80° C. in styropor;

stored in tubes in liquid nitrogen ($N_2$) at −180° C.

The invention claimed is:

1. A process for the production of dedifferentiated, programmable cells of human monocytic origin, comprising:
   a) isolating monocytes from human blood;
   b) attaching said monocytes to a culture vessel;
   c) propagating said monocytes attached to said culture vessel in a culture medium comprising cellular growth factor M-CSF; and
   d) cultivating said monocytes simultaneously with or subsequently to step b) in a culture medium comprising IL-3.

2. The process according to claim 1, further comprising:
   d) obtaining dedifferentiated, programmable cells of human monocytic origin after said cultivating said monocytes simultaneously with or subsequently to step b) in a culture medium comprising IL-3.

3. The process according to claim 2, wherein said culture medium comprising IL-3 further comprises a mercapto compound.

4. The process according to claim 3, wherein said mercapto compound has at least one carbon group bonded to the sulfur, and wherein hydrocarbon groups may be substituted with one or more functional groups.

5. The process according to claim 4, wherein said mercapto compound is 2-mercaptoethanol or dimethylsulfoxide.

6. The process according to claim 2, further comprising contacting the cells with a biologically acceptable organic solvent.

7. The process according to claim 6, wherein said biologically acceptable organic solvent is added after said cultivation of said monocytes in a culture medium containing IL-3 but before said obtaining dedifferentiated, programmable cells of human monocytic origin from said culture medium comprising IL-3.

8. The process according to claim 7, wherein said biologically acceptable organic solvent is an alcohol with 1-4 carbon atoms.

9. The process according to claim 8, wherein said biologically acceptable alcohol is ethanol.

10. The process according to claim 6, wherein said dedifferentiated, programmable cells of human monocytic origin are brought into contact with the vapor phase of said biologically acceptable organic solvent.

11. The process according to claim 2, further comprising suspending said dedifferentiated, programmable cells of human monocytic origin in a suitable cell culture medium subsequent to step d).

12. The process according to claim 11, wherein said suspension medium is RPMI or DMEM.

13. The process according to claim 11, wherein said suspension medium comprises a cytokine or LIF.

14. The process according to claim 2, wherein, subsequent to step d), said dedifferentiated, programmable cells of human monocytic origin are suspended in a liquid medium and subsequently deep-frozen.

15. A process for the production of dedifferentiated, programmable cells of human monocytic origin in a pharmaceutical preparation, comprising:
   a) isolating monocytes from human blood;
   b) attaching said monocytes to a culture vessel;
   c) propagating said monocytes attached to said culture vessel in a culture medium comprising cellular growth factor M-CSF;
   d) cultivating said monocytes simultaneously with or subsequently to step b) in a culture medium comprising IL-3;

e) obtaining dedifferentiated, programmable cell of human monocytic origin from said culture medium comprising IL-3; and f) formulating a pharmaceutical preparation in a suitable medium, wherein said pharmaceutical preparation is derived from said human adult dedifferentiated programmable cell.

16. A process for preparing a dedifferentiated, programmable cell of human monocytic origin for introduction into a body, comprising:

a) isolating monocytes from human blood;

b) attaching said monocytes to a culture vessel;

c) propagating said monocytes attached to said culture vessel in a culture medium comprising cellular growth factor M-CSF;

d) cultivating said monocytes simultaneously with or subsequently to step b) in a culture medium comprising IL-3;

e) obtaining dedifferentiated, programmable cells of human monocytic origin from said culture medium comprising IL-3; and f) applying said dedifferentiated, programmable cell of human monocytic origin to a material.

17. The process according to claim 16, wherein said material is an implantable material.

18. The process according to claim 17, wherein said implantable material is selected from the group consisting of cardiac valves, vessel prosthesis, bone prosthesis, joint prosthesis, bag, and chamber.

19. The process according to claim 16, wherein said material is a biodegradable matrix.

20. The process according to claim 1, wherein said dedifferentiated, programmable cells of human monocytic origin express a CD14 antigen and a CD90 antigen.

21. The process according to claim 15, wherein said dedifferentiated, programmable cells of human monocytic origin express a CD14 antigen and a CD90 antigen.

22. The process according to claim 16, wherein said dedifferentiated, programmable cell of human monocytic origin expresses a CD14 antigen and a CD90 antigen.

* * * * *